US011026732B2

(12) United States Patent
Allard et al.

(10) Patent No.: US 11,026,732 B2
(45) Date of Patent: Jun. 8, 2021

(54) LIGAMENT FIXATION SYSTEM, IMPLANTS, AND DEVICES WITH A COMPRESSION CAP, AND METHODS OF USE

(71) Applicant: Paragon 28, Inc., Englewood, CO (US)

(72) Inventors: Randy Allard, Golden, CO (US); Albert Dacosta, Lone Tree, CO (US); Sean Gill, Denver, CO (US); Peter Andrew Mladinich, Lakewood, CO (US); Richard David Hunt, Arvada, CO (US); Frank S. Bono, Castle Rock, CO (US); Benjamin Majors, Englewood, CO (US)

(73) Assignee: Paragon 28, Inc., Englewood, CO (US)

( * ) Notice: Subject to any disclaimer, the term of this patent is extended or adjusted under 35 U.S.C. 154(b) by 0 days.

(21) Appl. No.: 16/512,807

(22) Filed: Jul. 16, 2019

(65) Prior Publication Data

US 2019/0336190 A1 Nov. 7, 2019

Related U.S. Application Data

(63) Continuation of application No. PCT/US2018/057554, filed on Oct. 25, 2018.
(Continued)

(51) Int. Cl.
*A61B 17/86* (2006.01)
*A61F 2/08* (2006.01)
*A61B 17/68* (2006.01)

(52) U.S. Cl.
CPC ........ *A61B 17/8685* (2013.01); *A61B 17/863* (2013.01); *A61B 17/8645* (2013.01);
(Continued)

(58) Field of Classification Search
CPC ............ A61B 17/0401; A61B 17/8685; A61B 2017/681
See application file for complete search history.

(56) References Cited

U.S. PATENT DOCUMENTS

| | | | |
|---|---|---|---|
| 3,343,443 A * | 9/1967 | Moore | F16B 25/0031 411/5 |
| 3,953,896 A | 5/1976 | Treace | |

(Continued)

FOREIGN PATENT DOCUMENTS

| | | |
|---|---|---|
| CN | 102670291 | 9/2012 |
| CN | 102920498 | 2/2013 |

(Continued)

OTHER PUBLICATIONS

Porucznik, "Screw vs. tightrope fixation for syndesmotic fractures," AAOS Now, http://www.aaos.org/news/aaosnow/may08/clinical4.asp, 3 pages, May 2008.

(Continued)

*Primary Examiner* — Christian A Sevilla
(74) *Attorney, Agent, or Firm* — Heslin Rothenberg Farley & Mesiti P.C.

(57) ABSTRACT

Implants, devices, systems, and methods for achieving ligament fixation are disclosed. An implant comprises a cap member comprising an internally threaded opening extending from a first end thereof, an anchor portion comprising a first end that defines a tip of the implant and external threads, and a coupling portion extending between the cap member and the anchor portion. The coupling portion of the implant includes an externally threaded portion threadably coupled within the internally threaded opening of the cap member. The cap member of the implant is longitudinally moveable along the coupling portion. Insertion instruments for inserting an implant for ligament fixation are also disclosed.

(Continued)

Methods of using an implant for achieving ligament fixation are also disclosed.

18 Claims, 12 Drawing Sheets

Related U.S. Application Data

(60) Provisional application No. 62/576,946, filed on Oct. 25, 2017.

(52) U.S. Cl.
CPC .......... *A61F 2/0805* (2013.01); *A61F 2/0811* (2013.01); *A61B 2017/681* (2013.01); *A61F 2002/0829* (2013.01); *A61F 2002/0882* (2013.01); *A61F 2210/0004* (2013.01); *A61F 2220/0033* (2013.01); *A61F 2220/0075* (2013.01); *A61F 2250/0012* (2013.01)

(56) References Cited

U.S. PATENT DOCUMENTS

| | | | |
|---|---|---|---|
| 4,955,910 A | 9/1990 | Bolesky | |
| 5,004,474 A | 4/1991 | Fronk | |
| 5,061,137 A | 10/1991 | Gourd | |
| 5,152,790 A | 10/1992 | Rosenberg | |
| 5,486,197 A | 1/1996 | Le | |
| 5,507,812 A | 4/1996 | Moore | |
| 5,968,045 A | 10/1999 | Frazier | |
| 5,971,987 A * | 10/1999 | Huxel | A61B 17/8605 411/2 |
| 6,187,008 B1 | 2/2001 | Hamman | |
| 6,461,373 B2 | 10/2002 | Wyman | |
| 6,652,592 B1 | 11/2003 | Grooms | |
| 6,921,402 B2 | 7/2005 | Contiliano | |
| 7,235,078 B2 | 6/2007 | West, Jr. | |
| 7,235,091 B2 | 6/2007 | Thornes | |
| 7,608,098 B1 | 10/2009 | Stone | |
| 7,625,395 B2 | 12/2009 | Mückter | |
| 7,727,278 B2 | 6/2010 | Olsen | |
| 7,955,388 B2 | 6/2011 | Jensen | |
| 8,128,696 B2 | 3/2012 | Mayr | |
| 8,439,976 B2 | 5/2013 | Albertorio | |
| 8,696,716 B2 | 4/2014 | Kartalian et al. | |
| 8,696,719 B2 | 4/2014 | Lofthouse | |
| 8,753,380 B2 * | 6/2014 | Cheng | A61B 17/8605 606/306 |
| 8,858,605 B1 * | 10/2014 | Glatzer | A61B 17/7037 606/307 |
| 8,864,804 B2 | 10/2014 | Champagne | |
| 9,138,219 B2 * | 9/2015 | Horrell | A61B 17/86 |
| 9,358,055 B2 * | 6/2016 | Cheng | A61B 17/863 |
| 2004/0172032 A1 | 9/2004 | Jackson | |
| 2005/0059972 A1 | 3/2005 | Biscup | |
| 2007/0162124 A1 | 7/2007 | Whittaker | |
| 2007/0218750 A1 * | 9/2007 | Corrao | A61B 17/8605 439/404 |
| 2007/0282342 A1 | 12/2007 | Niederberger | |
| 2008/0182227 A1 | 7/2008 | Wolf | |
| 2009/0198287 A1 | 8/2009 | Chiu | |
| 2009/0306777 A1 | 12/2009 | Widmer | |
| 2011/0040335 A1 | 2/2011 | Stihl et al. | |
| 2011/0276099 A1 | 11/2011 | Champagne | |
| 2012/0123474 A1 | 5/2012 | Zajac | |
| 2012/0150237 A1 | 6/2012 | Combrowski | |
| 2012/0172936 A1 | 7/2012 | Horrell | |
| 2012/0209332 A1 * | 8/2012 | Janowski | A61B 17/7082 606/278 |
| 2012/0271416 A1 | 10/2012 | Mackay | |
| 2013/0030480 A1 | 1/2013 | Donate | |
| 2013/0090691 A1 | 4/2013 | Zhang et al. | |
| 2013/0131737 A1 * | 5/2013 | Cheng | A61B 17/863 606/316 |
| 2013/0184708 A1 | 7/2013 | Robinson et al. | |
| 2013/0317503 A1 * | 11/2013 | Songer | A61B 17/8635 606/66 |
| 2014/0025166 A1 | 1/2014 | Bonutti | |
| 2014/0121711 A1 | 5/2014 | Worcel | |
| 2014/0214095 A1 | 7/2014 | Rosenwasser et al. | |
| 2014/0228866 A1 | 8/2014 | Fallin et al. | |
| 2014/0243977 A1 | 8/2014 | Tepic | |
| 2014/0276894 A1 | 9/2014 | Ramsay et al. | |
| 2015/0051601 A1 | 2/2015 | Larsen et al. | |
| 2015/0073475 A1 | 3/2015 | Schaller | |
| 2015/0081019 A1 | 3/2015 | Whittaker | |
| 2016/0045636 A1 | 2/2016 | Rizk et al. | |
| 2016/0287302 A1 | 10/2016 | Horrell et al. | |
| 2016/0354183 A1 | 12/2016 | Montero | |
| 2016/0367303 A1 | 12/2016 | Mahajan et al. | |
| 2016/0367341 A1 | 12/2016 | Perez Yanini | |
| 2017/0079698 A1 | 3/2017 | Fallin et al. | |
| 2018/0092681 A1 | 4/2018 | Lutz | |
| 2019/0083232 A1 | 3/2019 | DaCosta et al. | |
| 2019/0336270 A1 | 11/2019 | Dacosta et al. | |

FOREIGN PATENT DOCUMENTS

| | | |
|---|---|---|
| GR | 20090100297 | 12/2010 |
| WO | 2010121234 | 10/2010 |

OTHER PUBLICATIONS

Xu et al., "Flexible fixation of syndesmotic diastasis using the assembled bolt-tightrope system," Scandinavian Journal of Trauma, Resuscitation and Emergency Medicine, vol. 21(71), 9 pages, 2013.

"Interventional procedure overview of suture fixation of acute disruption of the distal tibiofibular syndesmosis," National Institute for Health and Care Excellence, www.nice.org.uk, 43 pages, Jul. 2014.

International Search Report and Written Opinion of the International Searching Authority for PCT/US2018/051349, dated Dec. 3, 2018, 8 pages.

International Search Report and Written Opinion of the International Searching Authority for PCT/US2018/055028, dated Jan. 2, 2019, 12 pages.

International Search Report and Written Opinion of the International Searching Authority for PCT/US2018/057554, dated Jan. 17, 2019, 8 pages.

International Preliminary Report on Patentability for International Application No. PCT/US2018/057554, dated Apr. 28, 2020, 5 pages, International Bureau of WIPO.

International Search Report and Written Opinion of the International Searching Authority for PCT/US2020/050438, dated Dec. 10, 2020, 8 pages.

\* cited by examiner

LIGAMENT FIXATION SYSTEM, IMPLANTS, AND DEVICES WITH A COMPRESSION CAP, AND METHODS OF USE

CROSS-REFERENCE TO RELATED APPLICATION

This application is a continuation of PCT international patent application No. PCT/US2018/057554, filed Oct. 25, 2018, entitled Ligament Fixation System, Implants, and Devices with a Compression Cap, and Methods of Use, which claims the benefit of U.S. provisional application No. 62/576,946, filed Oct. 25, 2017, entitled Ligament Fixation System, Implants, and Devices with a Compression Cap, and Methods of Use, which are hereby incorporated herein by reference in their entireties.

TECHNICAL FIELD

The present invention relates generally to general, podiatric, and orthopaedic surgery related to fixation of ligaments. More specifically, but not exclusively, the present invention relates to ligament fixation implants, devices, and systems with compression caps, as well as insertion instruments and methods for achieving ligament fixation.

BACKGROUND OF THE INVENTION

Syndesmotic injuries are a result of trauma (not specific to sports injuries) and can occur as a purely ligamentous injury or in combination with an ankle fracture. These ligaments become disrupted, separated, or injured where semi-constrained approximation and fixation is needed to aide in healing without the need for a second surgery, such as removal of a rigid fixation screw. The current standard of care for syndesmotic injuries involves either rigid fixation with a screw, or a tether-based constraint across the entire width of the ankle (TightRope, etc.).

The more rigid screw-based fixation is simple to implant and stabilizes the joint, but fails to allow any motion at all, as would normally exist physiologically. This limits the patient's range of motion, and unpredictable screw failure locations can result in damage to existing bone and patient pain.

Tethered constraints, such as the Arthrex Tightrope, do allow for motion of the joint, but by spanning the entire width of the ankle, fail to mimic the intact ligament structures of the syndesmosis in terms of attachment location and distance between the tibia and fibula. However, tethered constraints result in a necessary decrease in structural strength due to the associated surgical technique of, for example, the Tightrope, and for these devices which involve drilling a hole through both the tibia and fibula which remains unfilled by structural material (e.g. a metal screw).

Thus, new and improved devices, systems, and methods for achieving ligament fixation are needed to overcome the above-noted drawbacks of the currently available solutions for addressing syndesmotic injuries.

SUMMARY OF THE INVENTION

The present disclosure is directed toward devices and methods for use in ligament fixation. The devices, systems, and methods for achieving ligament fixation.

In one aspect of the present disclosure provided herein, is an implant. The implant including an end member, an anchor member coupled to the end member, and a cap member removably coupled to the end member.

In another aspect of the present disclosure provided herein, is a method for inserting an implant. The method includes obtaining the implant. The implant includes an end member, an anchor member coupled to the end member, and a cap member removably coupled to the end member. The method also includes engaging the end member with an insertion instrument and inserting the coupled end member and anchor member into a patient to position the end member in a first bone and the anchor member in a second bone. The method further includes inserting the cap member over the end member to compress the first bone and the second bone.

In yet another aspect of the present disclosure provided herein, is a system. The system including an implant and an insertion instrument for coupling to the implant. The implant including an end member, an anchor member coupled to the end member, and a cap member removably coupled to the end member.

In another aspect of the present disclosure, an implant is provided. The implant comprises a cap member comprising an internally threaded opening extending from a first end thereof, an anchor portion comprising a first end that defines a tip of the implant and external threads, and a coupling portion extending between the cap member and the anchor portion. The coupling portion includes an externally threaded portion threadably coupled within the internally threaded opening of the cap member. The cap member is longitudinally moveable along the coupling portion.

In some embodiments, the coupling portion comprises a breakaway portion. In some such embodiments, the breakaway portion is comprised of a circumferential groove. In some embodiments, the coupling portion is of one-piece construction. In some embodiments, the cap member, the anchor portion and the coupling portion are integral. In some embodiments, the coupling portion comprises a torque application feature comprising outer planar surfaces circumferentially arranged about the coupling portion. In some embodiments, the cap member comprises a shaft portion that defines the first end of the cap member and includes the internally threaded opening, and an enlarged head portion extending from the shaft portion that defines a second end of the cap member, the second end of the cap member defining a free end of the implant that opposes the tip of the implant.

In some embodiments, the cap member further comprises a non-circular drive opening extending from the second end thereof. In some embodiments, the anchor portion comprises a shaft portion with a first end and a second end, a proximal coupling portion extending from the first end of the shaft portion of the anchor member to the coupling portion, and a distal portion extending from the second end of the shaft portion of the anchor member. In some such embodiments, at least a portion of the shaft portion of the anchor member comprises the external threads. In some such embodiments, the proximal coupling portion is void of external threads.

In some embodiments, the distal portion comprises at least one surface feature positioned proximate to the first end of the anchor member. In some such embodiments, the at least one surface feature comprises at least one cutting flute. In some embodiments, the at least one surface feature comprises a plurality of circumferentially arranged longitudinally extending flutes.

In some embodiments, the coupling portion comprises a coupling member coupled to the anchor portion and an end member coupled to the coupling member. In some such embodiments, the coupling member and the end member are separate and distinct components. In some embodiments, the coupling member is made of a bioresorbable material. In some embodiments, the end member comprises the externally threaded portion threadably coupled within the internally threaded opening of the cap member such that cap member is longitudinally moveable along the end member of the coupling portion. In some such embodiments, the anchor portion comprises a second engagement end that opposes the first end thereof and engages a first engagement end of the coupling member. In some such embodiments, each of the second engagement end of the anchor portion and the first engagement end of the coupling member include at least one projection and at least one recess, and the at least one projection of the second engagement end of the anchor portion is positioned within the at least one recess of the first engagement end of the coupling member, and the at least one projection of the first engagement end of the coupling member is positioned within the at least one recess of the second engagement end of the anchor portion.

In some embodiments, the coupling member comprises a second engagement end that opposes the first engagement thereof and engages a first engagement end of the end member. In some such embodiments, each of the second engagement end of the coupling member and the first engagement end of the end member include at least one projection and at least one recess, and the at least one projection of the second engagement end of the coupling member is positioned within the at least one recess of the first engagement end of the coupling member, and the at least one projection of the first engagement end of the coupling member is positioned within the at least one recess of the second engagement end of the coupling member.

In some embodiments, the end member comprises a torque application feature comprising outer planar surfaces circumferentially arranged about the end member. In some embodiments, the anchor portion, the coupling member and the end member each include a cannulated opening that are aligned to form a through hole through the implant. In some such embodiments, the implant further comprises a tension member positioned within the through hole and including a first portion coupled to the end member and a second portion coupled to the anchor member. In some embodiments, the tension member is elastic. In some embodiments, the tension member comprises a braided suture.

In some embodiments, the second portion of the tension member is coupled to the anchor member via at least one pin. In some such embodiments, the anchor member further comprises at least one transverse opening extending from an exterior surface portion of the anchor member to the cannulated opening thereof, and the at least one pin is positioned within the at least one transverse opening and extends into the cannulated opening and in abutment with the second portion of the tension member. In some such embodiments, the at least one pin positioned within the at least one transverse opening and in abutment with the tension member couples the second portion of the tension member and the anchor portion together. In some such embodiments, the anchor member further comprises at least one slot extending at least partially through the anchor member from an interior surface of the anchor member that forms the cannulated opening thereof, the at least one slot being aligned with the at least one transverse opening such that the at least one pin positioned within the at least one transverse opening deforms the second portion of the tension member into the at least one slot to couple the second portion of the tension member and the anchor portion together.

In some embodiments, the first portion of the tension member is coupled to the end member via a pin extending at least partially through the end member and into the cannulated opening thereof and into abutment with the first portion of the tension member. In some embodiments, the first portion of the tension member is coupled to the end member via an internal crimp ferrule.

In some embodiments, the cap member comprises a shaft portion that defines the first end of the cap member and includes the internally threaded opening, and an enlarged head portion extending from the shaft portion that defines the second end of the cap member and includes a non-circular drive opening extending into the second end. In some embodiments, the anchor portion comprises a shaft portion with a first end and a second end, a proximal coupling portion extending from the first end of the shaft portion of the anchor member to the coupling portion, and a distal portion extending from the second end of the shaft portion of the anchor member. In some such embodiments, at least a portion of the shaft portion of the anchor member comprises the external threads. In some such embodiments, the proximal coupling portion is void of external threads. In some embodiments, the distal portion comprises at least one surface feature positioned proximate to the first end of the anchor portion. In some such embodiments, the at least one surface feature comprises at least one cutting flute. In some such embodiments, the at least one surface feature comprises a plurality of circumferentially arranged longitudinally extending flutes.

In another aspect of the present disclosure, a method for inserting an implant is provided. The method comprises obtaining the implant. The implant comprises a cap member comprising an internally threaded opening extending from a first end thereof, an anchor portion comprising a first end that defines a tip of the implant and external threads, and a coupling portion coupled to the anchor portion, the coupling portion including an externally threaded portion. The method further comprises engaging the coupling portion with an insertion instrument. The method also comprises inserting the coupled coupling portion and anchor member into a patient to position the coupling member at least partially in a first bone and the anchor member in a second bone. The method further comprises threadably engaging the externally threaded portion of the coupling portion within the internally threaded opening of the cap member and longitudinally translating the cap member along the coupling portion toward the anchor portion to such an extent that the cap member engages the second bone and the implant compresses the first and second bones together. Longitudinally translating the cap member along the coupling portion comprises rotating the cap member about the coupling portion.

In some embodiments, the implant comprises an implant as disclosed above. In some embodiments, the first bone is a fibula and the second bone is a tibia. In some embodiments, the anchor portion and the coupling portion are integral during insertion.

In some embodiments, the method further comprises adjusting the longitudinal position of the cap member after the inserting to adjust the compression of the first and second bones, the adjusting the longitudinal position of the cap member comprises further rotating the cap member about the coupling portion such that at least a portion of the compression between the first and second bones is released In some such embodiments, the adjusting the longitudinal position of the cap member comprising releasing at least a portion of the compression between the first and second bones.

In another aspect of the present disclosure, a system is provided. The system comprises an implant comprising an implant as disclosed above, and an insertion instrument for coupling to the implant and rotating the implant about an axis of the implant.

In some embodiments, the system further comprises a plate with at least one aperture extending therethrough, and wherein the entirety of the anchor portion, the entirety of the coupling portion and only a portion of the cap member are configured to pass through the at least one aperture of the implant These and other objects, features and advantages of this invention will become apparent from the following detailed description of the various aspects of the invention taken in conjunction with the accompanying drawings.

BRIEF DESCRIPTION OF THE DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

DETAILED DESCRIPTION FOR CARRYING OUT THE INVENTION

Figure 1:
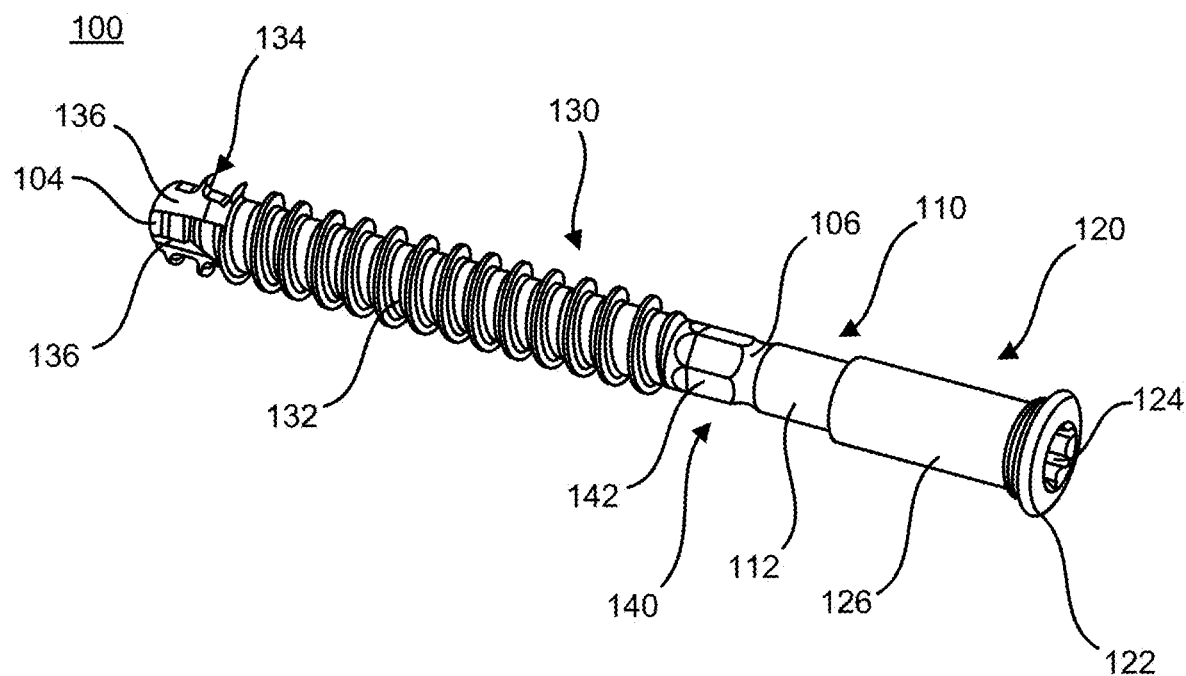
FIG. 1 is a side perspective view of one embodiment of an implant, in accordance with an aspect of the present disclosure.
Figure 2:
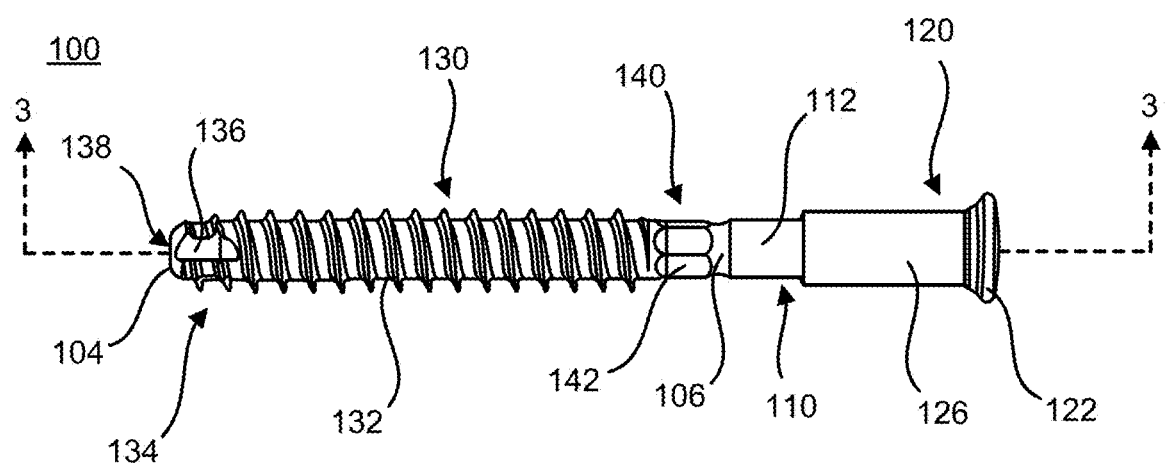
FIG. 2 is a side view of the implant of FIG. 1, in accordance with an aspect of the present disclosure.

Generally stated, disclosed herein are implants, devices and systems with a compression cap for achieving ligament fixation. Further, methods for using the implants, devices and systems to achieve ligament fixation are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation and methods are described herein with reference to use with the bones of the ankle, the bones of the foot, ankle and lower leg may be used to describe the surfaces, positions, directions or orientations of the implants, devices, instrumentation and methods. Further, the implants, devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation and methods, and the aspects, components, features and the like thereof, described herein with respect to the left leg may be mirrored so that they likewise function with the right leg. Further, the implants, devices, instrumentation and methods, and the aspects, components, features and the like thereof, disclosed herein are described with respect to the leg for brevity purposes, but it should be understood that the implants, devices, instrumentation and methods may be used with other bones of the body having similar structures.

Referring to the drawings, wherein like reference numerals are used to indicate like or analogous components throughout the several views, and with particular reference to FIGS. 1-6 there is illustrated an implant 100 and FIGS. 13-19 there is illustrated an implant 300. The implants 100, 300 may be, for example, supportive enough to heal syndesmotic ligaments post-operatively. The implants 100, 300 may also, for example, selectively constrain motion in all directions to allow for the ligaments to heal. After the syndesmotic ligaments heal, the implants 100, 300 allows for physiologic motion. The components of the implants 100, 300 may be made of, for example, titanium, stainless steel, polymers, resorbable or time release materials, or another like material as known by one of ordinary skill in the art. In addition, the implant 300 may be made of, for example, polyester or UHMWPE suture, resorbable suture, co-braids thereof, thermoplastic urethane bumper, and other resorbable time release materials or polymers. The implant 100, 300 may also re-create pressure in the lateral gutter. The surgical methods include drilling a hole through both the fibula and tibia and then inserting an implant 100, 300 to fill the created bone cavities to provide a stronger post-op construct.

Referring now to FIGS. 1-6 and 10-12, the implant 100 is illustrated. In addition to the above, the implant 100 also allows for screw-like implantation and temporary rigid fixation, then, after insertion, the implant 100 is designed to break away at a specific location after a period of non-weight bearing. The temporary rigid fixation of the implant 100 gives the fixed joint time to stabilize through healing and then allows physiologic motion after the breakaway occurs. The breakaway location is set in the space or gap between the fibula and tibia, where the subsequent risk of damage to native bone is lower.

Figure 3:
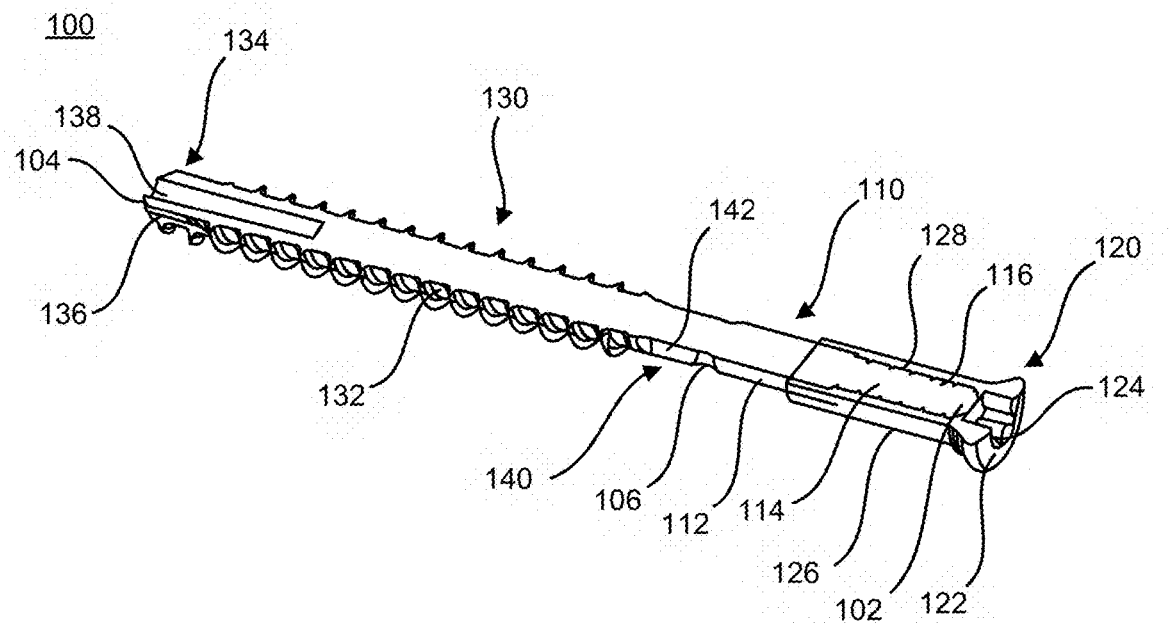
FIG. 3 is a perspective, cross-sectional view of the implant of FIG. 1 taken along line 3-3 in FIG. 2, in accordance with an aspect of the present disclosure.

With continued reference to FIGS. 1-6 and 10-12, the implant 100 includes a proximal end 102 (see FIGS. 3-6), a distal end 104, and a breakaway portion 106 positioned between the proximal end 102 and the distal end 104. The implant 100 may also include an end member 110, a compression cap 120 removably coupled to the end member 110, and an anchor member 130. The breakaway portion 106 of the implant 100 may be positioned between the end member 110 and the anchor member 130. The end member 110 is coupled to the anchor member 130 by the breakaway portion 106. The breakaway portion 106 may be recessed into the exterior surface of the implant 100 to form a notch, groove, recess, necking or the like, as shown in FIGS. 1-6. The implant 100 may be, for example, a solid, monolithic, or one piece construct, as shown in FIG. 3. It is also contemplated that the implant 100 may optionally include, for example, a cannulated opening or through hole (not shown) which extends the entire length of the implant 100.

Figure 4:
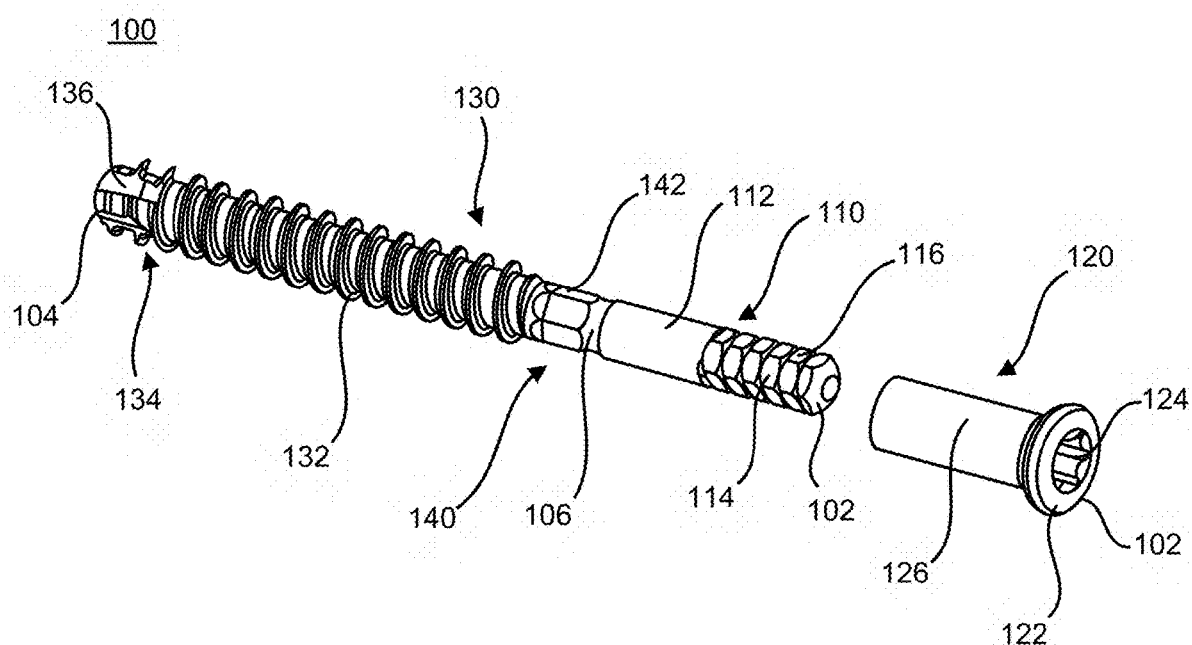
FIG. 4 is an exploded, first end perspective view of the implant of FIG. 1, in accordance with an aspect of the present disclosure.
Figure 5:
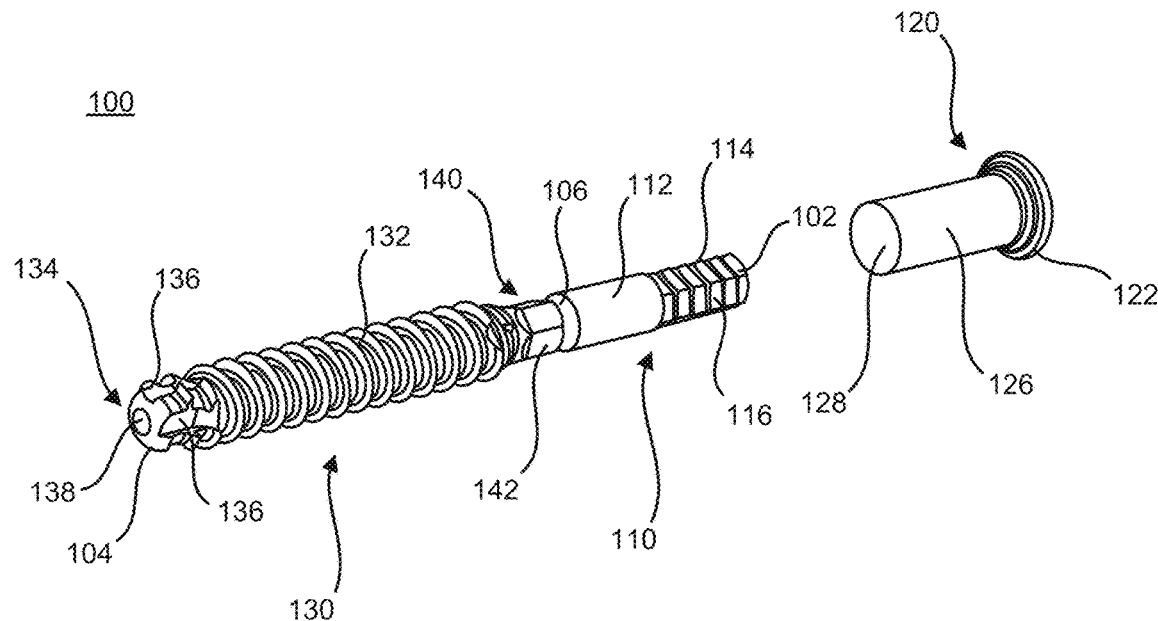
FIG. 5 is an exploded, second end perspective view of the implant of FIG. 1, in accordance with an aspect of the present disclosure.
Figure 6:
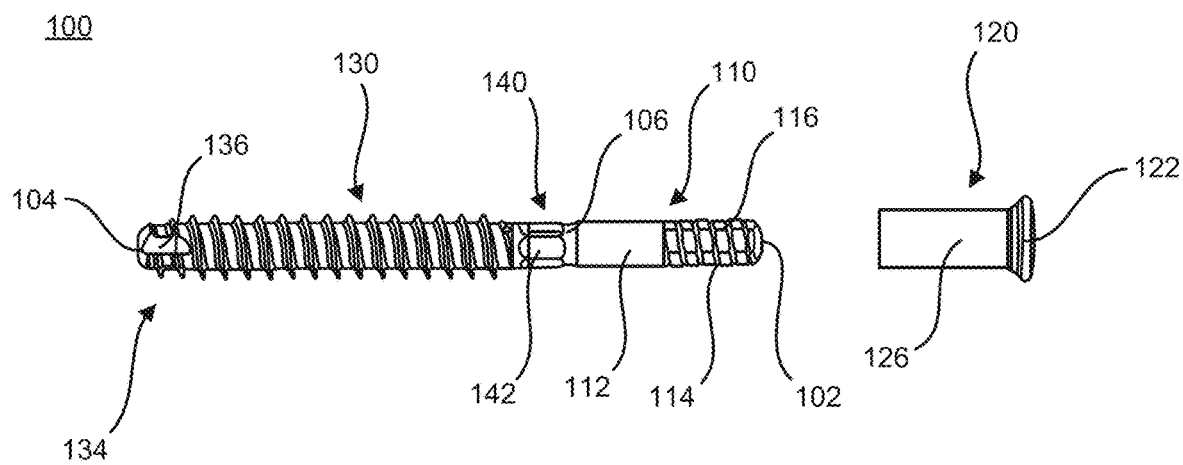
FIG. 6 is an exploded, side view of the implant of FIG. 1, in accordance with an aspect of the present disclosure.

With continued reference to FIGS. 3-6, the end member or fibula member 110 may include a proximal portion 114 and a distal portion 112. The proximal portion 114 may include, for example, threads from the proximal end 102 and extending toward the distal portion 112. The proximal portion 114 may also include at least one lateral removal member 116. The at least one lateral removal member 116 may be, for example, an external hexagonal drive feature, as shown in FIGS. 4-6. The at least one lateral removal member 116 may include surfaces for engaging an extraction instrument (not shown). The distal portion 112 may be coupled or connected to the breakaway notch 106 on a first side. The distal portion 112 may be, for example, a portion of the shaft member 116 which is smooth or lacks threads.

The anchor member or tibia member 130 may include a shaft portion or threaded portion 132, as shown in FIGS. 1-6. The shaft portion 132 may include an insertion end 134 at the second or distal end 104 of the implant 100 and the shaft portion 132. As shown in FIGS. 1-6, the anchor member 130 may also include a distal feature or portion 136 positioned at the insertion end 134 of the anchor member 130. The distal portion 136 may include surfaces for engaging an extraction instrument (not shown). The surfaces of the distal portion 136 may be, for example, cutting flutes or teeth, as shown in FIGS. 1-6. Alternatively, the surfaces of the distal portion 136 may form, for example, a hexagonal drive portion. The insertion end 134 of the anchor member 130 may also include, for example, an opening or recess 138 extending into the core of the anchor member 130 along at least a portion of the longitudinal axis of the implant 100, as shown in FIG. 3. In an embodiment of the anchor member 130 including a cannulation (not shown), the opening 138 may be, for example, continuous or aligned with the cannulation.

The shaft portion 132 may also include a proximal coupling portion 140 at a first end of the shaft portion 132 opposite the insertion end 134. The proximal coupling portion 140 is connected to the breakaway portion 106 on a second side opposite the distal portion 112 of the end member 110. The proximal coupling portion 140 may be, for example, a section of the shaft portion 132 which lacks threads and includes at least one lateral removal member 142. The at least one lateral removal member 142 may be, for example, an external hexagonal drive feature, as shown in FIGS. 1-6.

Figure 10:
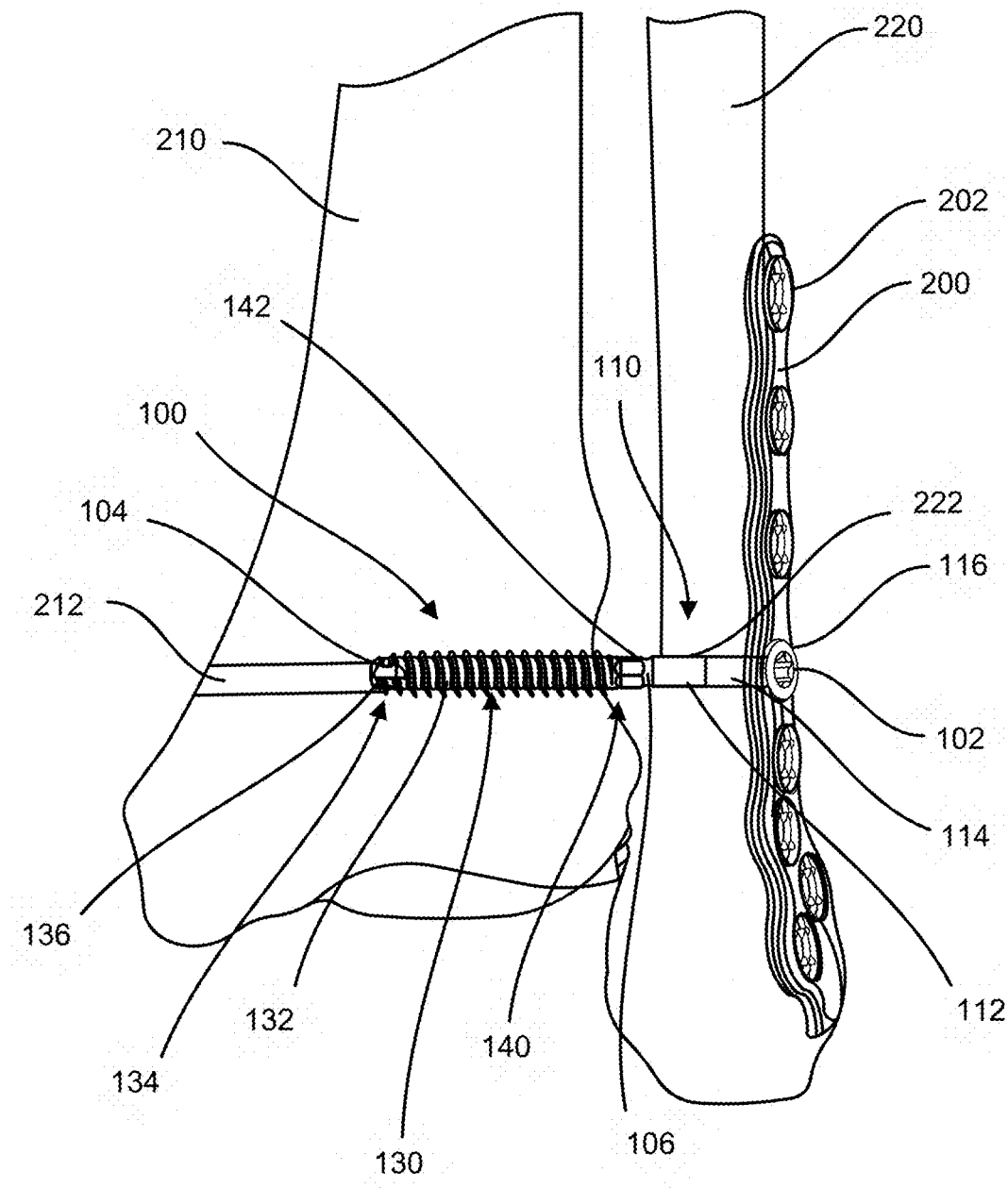
FIG. 10 is an anterior view of a portion of a left leg with a portion of the implant of FIG. 1 inserted into the bones of FIG. 7, in accordance with an aspect of the present disclosure.
Figure 11:
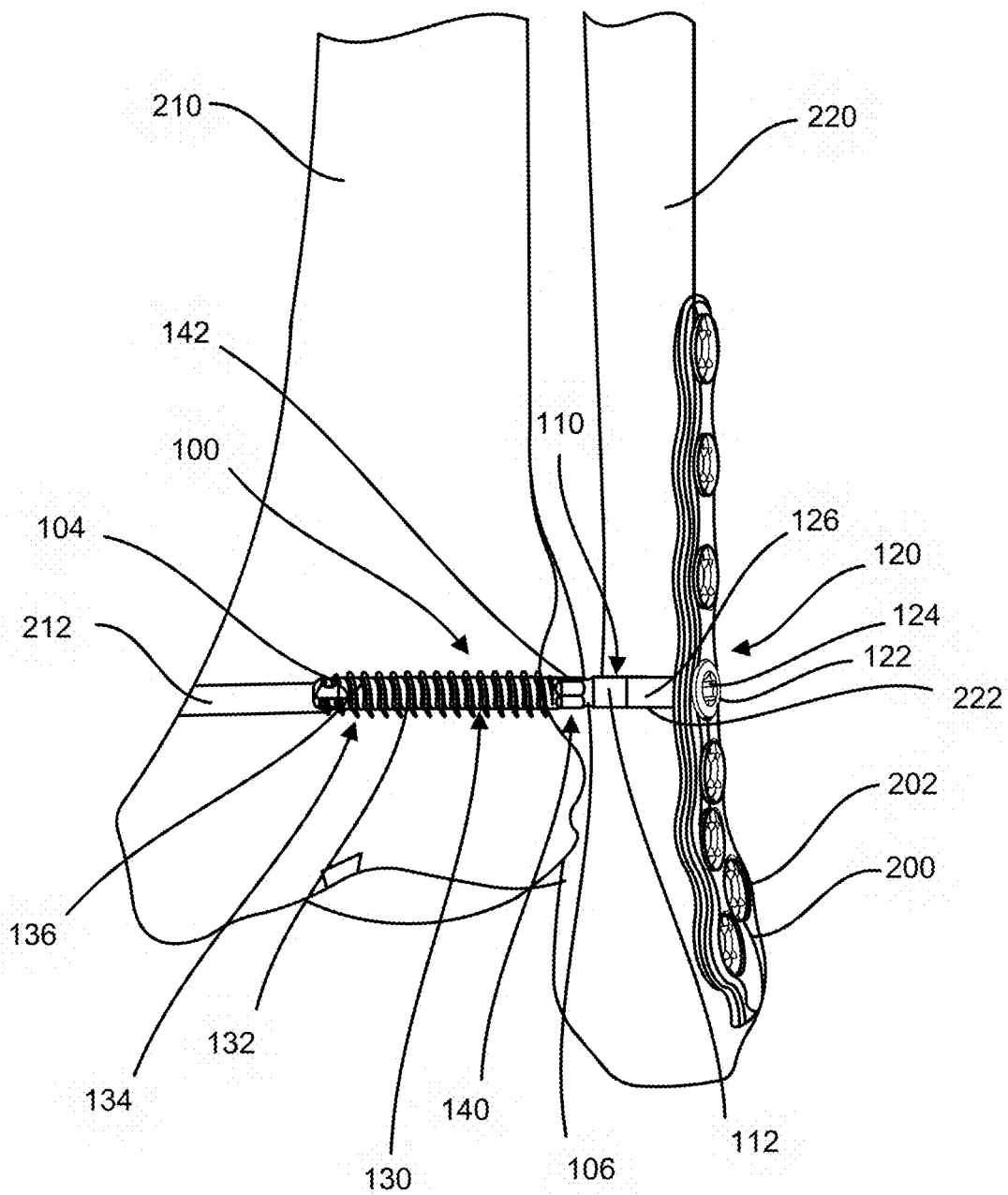
FIG. 11 is an anterior view of a portion of the left leg of FIG. 10 with the implant of FIG. 1 inserted into the bones of FIG. 7, in accordance with an aspect of the present disclosure.

As shown in FIGS. 1-6, the breakaway portion 106 may be, for example, a notch, groove, necking, or recess into the exterior surface of the implant 100. The notch, groove, necking, or recess may have, for example, a curved, rounded, or "V" shape. Alternatively, the breakaway portion 106 may be, for example, a resorbable material or member positioned between and coupling the end member 110 to the anchor member 130. The resorbable breakaway portion 106 may include, for example, a notch, groove, necking, or recess with a curved, rounded or "V" shape or, alternatively, the resorbable breakaway portion 106 may be flush with the exterior surface of the distal portion 112 and proximal coupling portion 140. The breakaway portion 106 may initially provide a connection between the end member 110 and anchor member 130 to constrain motion between the bones 210, 220, as shown in FIGS. 10 and 11. Then, once the breakaway portion 106 breaks or resorbs into the patient, the end member 110 and anchor member 130 will be separated and motion between the bones 210, 220 will no longer be constrained. When the implant 100 with the breakaway portion 106 breaks, the proximal end of the anchor member 130 may be, for example, smooth or flat. The implant 100 may have, for example, a breakaway feature ratio between breakaway notch 106 and the distal portion 112 of, for example, 64% to 89% and more preferably, 75% to 82%.

Although not shown it is also contemplated that the breakaway portion 106 may include, for example, an internal drive feature (not shown) for receiving an extraction instrument to remove the anchor member 130. The internal drive feature (not shown) may be, for example, a hexagonal or other multi-lobed drive opening. In addition, it is also contemplated that the breakaway portion 106 may also include, for example, at least one hole (not shown). The at least one hole (not shown) may be, for example, at least one through hole extending through the entire diameter of the implant 100 perpendicular to the longitudinal axis or alternatively, only through a portion of the implant 100. The holes (not shown) may be radially positioned, for example, between the distal portion 112 of the end member 110 and the proximal coupling portion 140 of the anchor member 130. In an embodiment, the breakaway portion 106 may include, for example, at least one channel (not shown) extending into the implant 100 from an exterior surface to form at least one blind hole, pocket or opening (not shown). In addition, the breakaway portion 106 may include an opening (not shown) positioned, for example, in the center of the anchor member 130 and extending into the anchor member 130 along the longitudinal axis of the implant 100. The breakaway portion 106 is designed or configured to fail at the precise location of the breakaway portion 106. Specifically, the materials and sizes of the implant 100 are selected to withstand a desired torsional force, bending moment, etc. at the breakaway portion 106. Alternative external and internal removal features that allow for engagement of an extraction instrument to remove the anchor member 130 from a lateral side of the patient are also contemplated.

With continued reference to FIGS. 1-6 and 10-12, the compression cap, fibula cap, cap 120 may include, for example, a head or button portion 122 at a first or proximal end and a shaft portion 126 extending away from an underside of the head portion 122. The head portion 122 may also include a tool engagement opening 124 positioned on a surface that is opposite the shaft portion 126, as shown in FIGS. 1, 3 and 4. The tool engagement opening 124 may have a multi-lobed shape, although other polygonal shapes are also contemplated, including a hexagonal shape or a hexalobular drive feature, for receiving an insertion tool. The cap 120 may also include an opening 128 extending into the shaft portion 126 from a second or distal end towards the head portion 122. The opening 128 may be, for example, threaded along at least a portion of the interior surface of the opening 128, as shown in FIG. 3. The threaded opening 128 may include threads that correspond to the threads on the threaded portion 114 of the fibula member 110, as shown in FIG. 3. The cap 120 may have, for example, a left-handed threaded attachment. The cap 120 may be, for example, moveable and may be actuated to compress the bones 210, 220 together. With continued reference to FIG. 3, the tool engagement opening 124 may be separated from the opening 128. Alternatively, it is also contemplated that the tool engagement opening 124 could, for example, extend to engage the opening 128 forming a through hole (not shown) within the cap 120. The through hole (not shown) may be, for example, configured to receive a guide pin, k-wire, or the like.

The implant 100 may have a length of, for example, approximately 40 mm to 70 mm. In an embodiment, the total length of the coupled end member 110 and cap 120 may remain constant and the length of the anchor member 130 may be variable to correspond to the varying size of a patient's bones 210, 220. Alternatively, in another embodiment, the coupled end member 110 and cap 120 may, for example, be available in multiple lengths to correspond to the varying size of a patient's bones 210, 220 and the length of the anchor member 130 may remain constant. In yet another embodiment, both the total length of the coupled end member 110 and cap 120 and the length of the anchor member 130 may be available in multiple lengths to allow for selection based on the size of the patient's bones 210, 220. The assembled end member 110 and cap 120 may have a length of, for example, between approximately 10 mm and 20 mm. The anchor member 130 may have a length of, for example, between approximately 20 mm and 60 mm.

Figure 7:
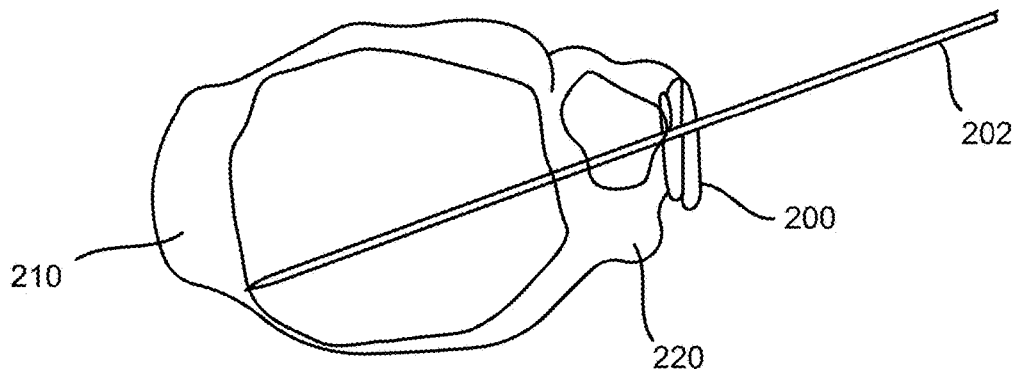
FIG. 7 is a distal, transverse planar view of a fibula and tibia with a k-wire inserted through a plate, the fibula and into the tibia, in accordance with an aspect of the present disclosure.
Figure 8:
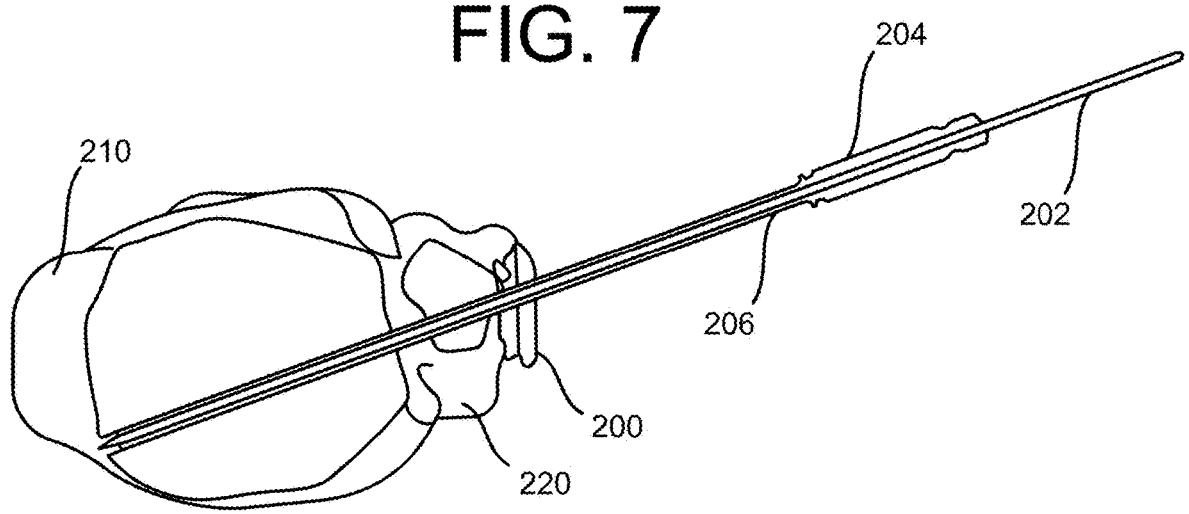
FIG. 8 is a distal, transverse planar view of the bones of FIG. 7 with a drill inserted over the k-wire of FIG. 7 through the plate, fibula and into the tibia, in accordance with an aspect of the present disclosure.
Figure 9:
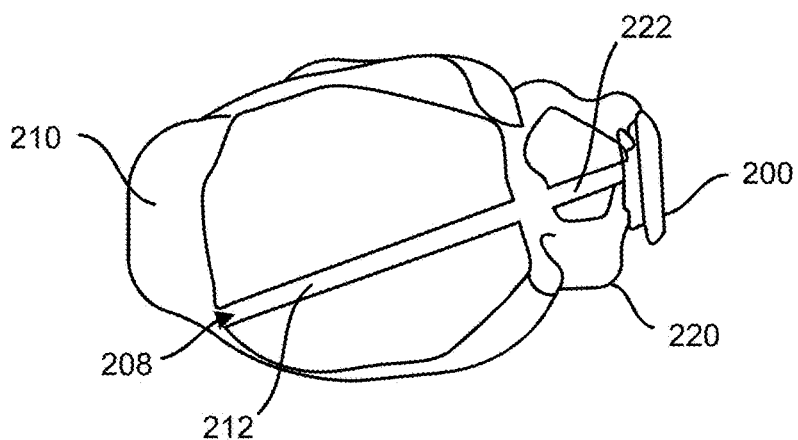
FIG. 9 is a distal, transverse planar view of the bones of FIG. 7 after the drill and k-wire are removed, in accordance with an aspect of the present disclosure.
Figure 12:
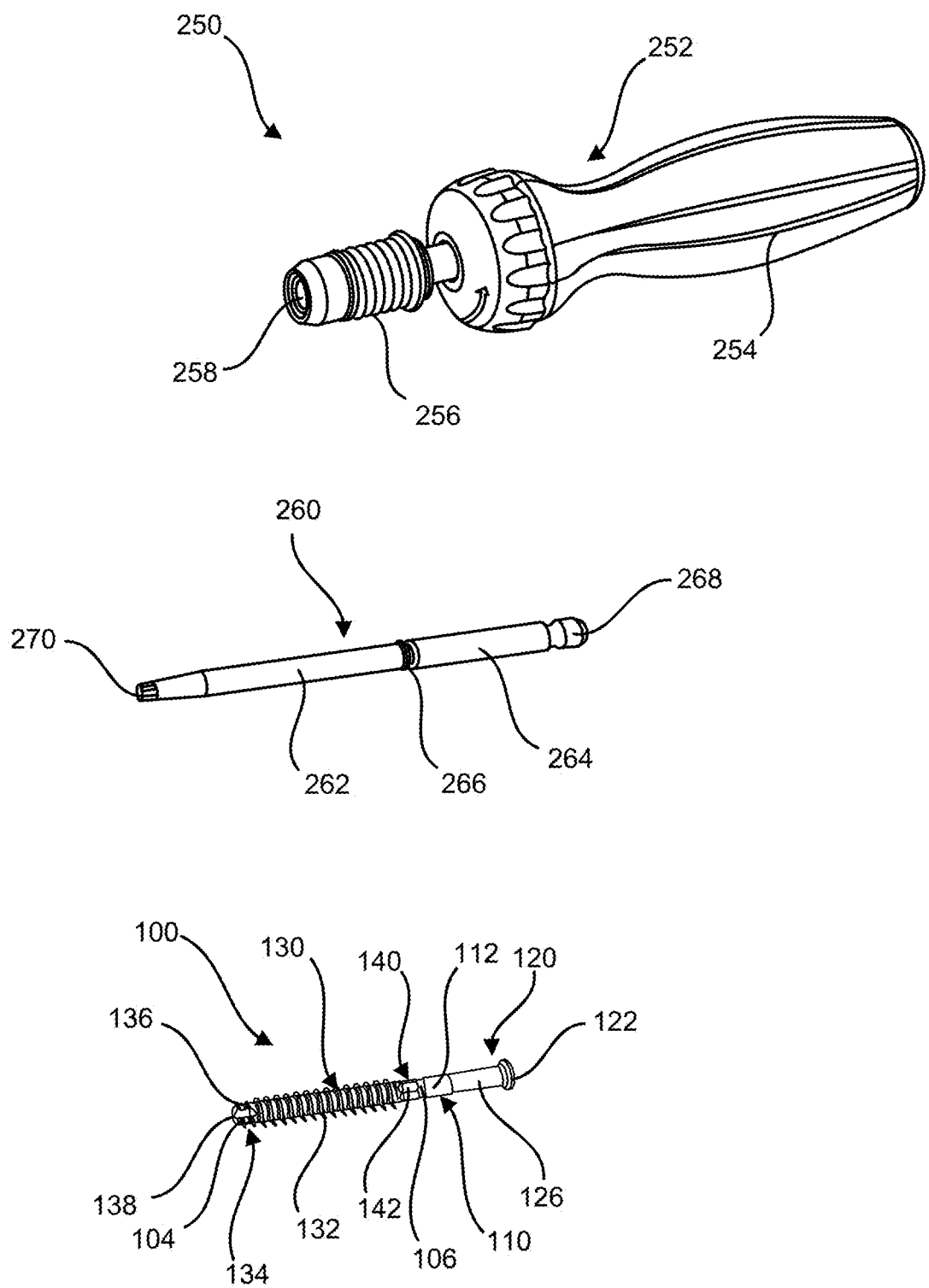
FIG. 12 is a side perspective view of a system including an insertion instrument and the implant of FIG. 1, in accordance with an aspect of the present disclosure.
Figure 13:
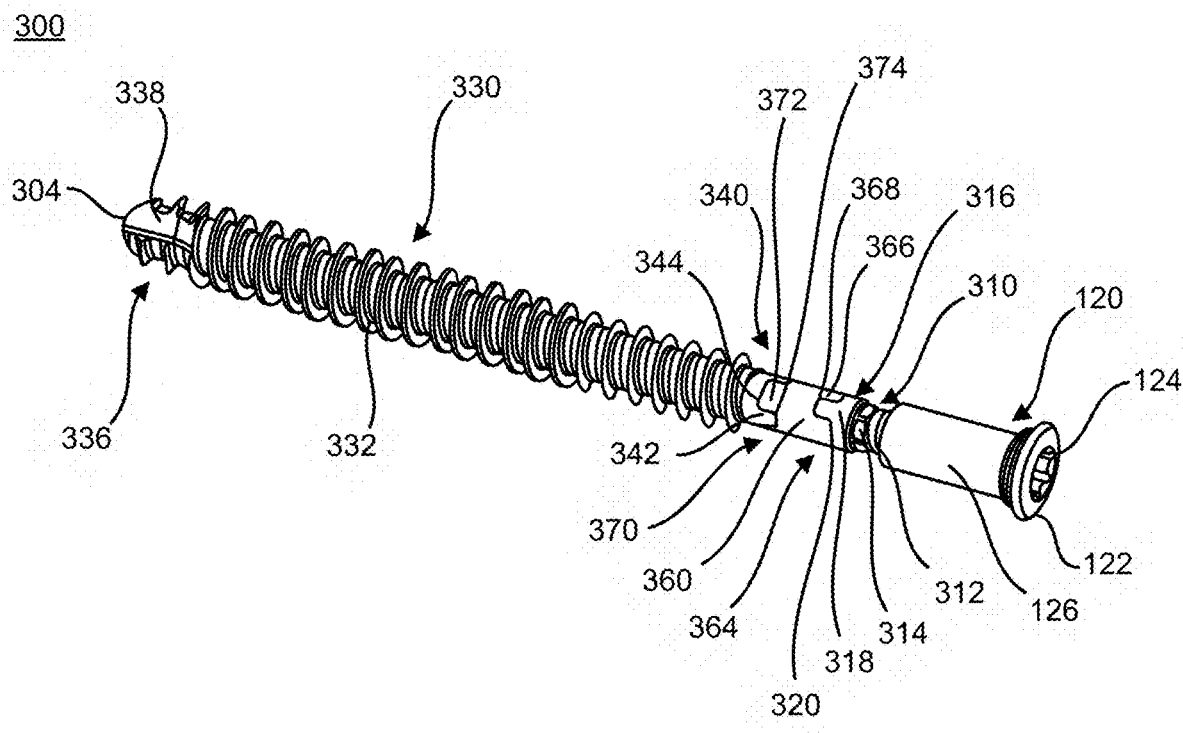
FIG. 13 is a side perspective view of another implant, in accordance with an aspect of the present disclosure.
Figure 14:
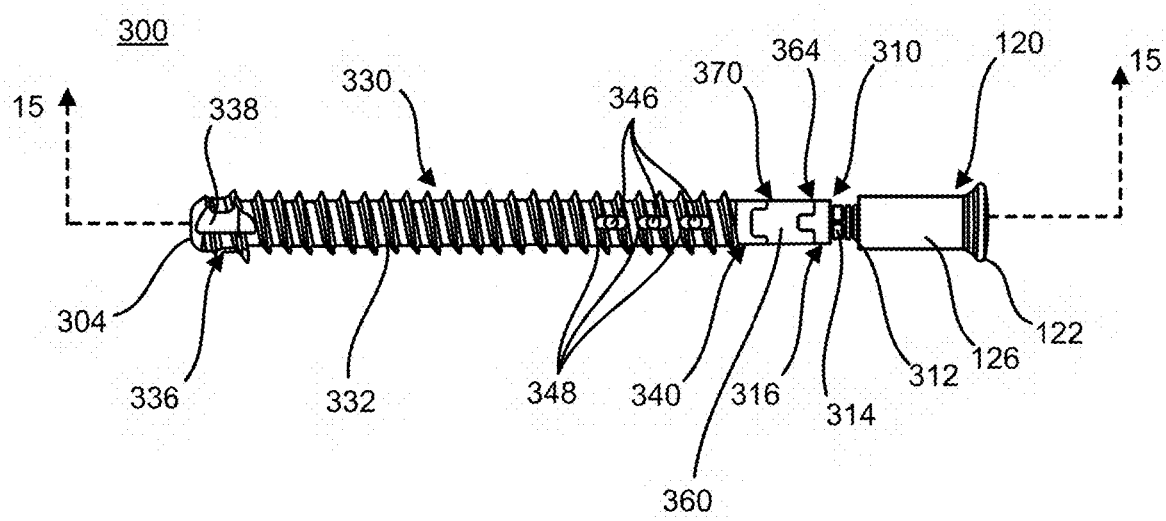
FIG. 14 is a side view of the implant of FIG. 13, in accordance with an aspect of the present disclosure.

Referring now to FIGS. 7-11, a method of inserting the implant 100 is shown. The method may optionally include positioning a plate 200 or washer (not shown) on a bone 220, for example, a fibula. The plate 200 or washer (not shown) may provide a buttress means for engaging the cap 120. The method may also include driving a k-wire or guide wire 202 through two bones 210, 220, for example, a fibula 220 and tibia 210, as shown in FIG. 7. If a plate 200 is used, the k-wire 202 may be inserted through an opening in the plate 200. Next, a drill bit 204 may be inserted over the k-wire 202 by aligning a cannulated opening 206 in the drill bit 204 with the k-wire 202, as shown in FIG. 8. The drill bit 204 may be used to drill openings 212, 222 through the bones 210, 220, as shown in FIG. 9. The openings 212, 222 may have a diameter, for example, that corresponds to the minor diameter or shaft of the anchor member 130. The openings 212, 222 may form an opening 208 for receiving the implant 100. After the opening 208 is drilled, the drill bit 204 and k-wire 202 may be removed from the bones 210, 220, as shown in FIG. 9. Optionally, after removing the drill bit 204 and prior to removing the k-wire 202, measurements of the opening 208 may be taken using a cannulated depth gauge (not shown) inserted over the k-wire 202. Once the measurements are taken, the k-wire 202 may then be removed. Alternatively, the k-wire 202 may be removed from the bones 210, 220 and a standard depth gauge (not shown) may be used to take the measurements. For example, an overall or first measurement of the opening or drill hole 208, such as a measurement to the far cortex of the tibia, may be taken using a cannulated depth gauge, standard depth gauge or other like instrument. The surgeon may also take a second measurement of the portion of the opening 208 in the fibula using, for example, a standard depth gauge or like instrument, to determine the size of the assembled end member 110 and cap 120. Then, a driver instrument (not shown) may be used to insert the coupled end member 110 and tibia member 130 of the implant 100 into the opening 208 in the bones 210, 220, as shown in FIG. 11. The implant 100 may be inserted to position the anchor member 130 in the tibia 210, the end member 110 in the fibula 220, and the breakaway notch 106 in a tibiofibular space or gap between the tibia 210 and fibula 220, as shown in FIG. 10. The space or gap may be, for example, approximately 3 mm. The torsional force applied to the end member 110 for inserting the implant 100 may be transmitted to the anchor member 130 through the breakaway portion 106. Next, the driver instrument (not shown) may be removed from the end member 110 of the implant 100 and a cap 120 may be inserted onto the end member 110. An insertion instrument 250, such as shown in FIG. 12, may be used to screw the cap 120 onto the threaded portion 114 of the end member 110. As the cap 120 is coupled to the end member 110, the head portion 122 contacts the fibula 220 or bone plate 200 and acts to compress the tibia 210 and fibula 220 with the inserted anchor member 130. Once the desired clear space or gap between the tibia 210 and fibula 220 and/or gutter pressure is achieved, the insertion instrument 250 may be removed from the tool engagement opening 124 in the cap 120 and the surgical procedure may be completed. During insertion of the cap 120, the torque may be, for example, measured or limited to facilitate a desired compression range between the bones 210, 220.

After inserting the implant 100, the cap 120 may be, for example, optionally adjusted to release some of the compression between the bones 210, 220 based on patient or doctor preference and/or surgical goal. Also, after inserting the implant 100, the breakaway portion 106 may eventually fail or fracture leaving the end member 110 separated from the anchor member 130 and the motion between the tibia 210 and fibula 220 no longer constrained. Once the breakaway portion 106 fails, the patient's physiologic motion is restored. Absent any further complications, the end member 110 and anchor member 130 may remain in the patient's fibula 220 and tibia 210, respectively. However, if hardware removal is required, the end member 110 may be removed from the fibula 220 after the breakaway portion 106 fractures. In addition, if necessary, the anchor member 130 may be removed from the tibia 210, as well. The anchor member 130 may be removed, for example, medially using the distal feature 136 or laterally using the at least one lateral removal member 142 of the proximal coupling portion 140.

A system including an insertion instrument 250 and implant 100 is shown in FIG. 12. The insertion instrument 250 includes a handle portion 252 and a driver bit 260 extending away from the handle portion 252. The handle portion 252 may include a handle 254 at a first end and a coupling portion 256 at a second end. The first end of the coupling portion 256 is attached to a proximal end of the handle 254. The coupling portion 256 may include an opening 258 extending into the coupling portion 256 from a second end. The opening 258 may be configured or sized and shaped to receive the driver bit 260. The driver bit 260 may include a first portion 262 at a first end and a second portion 264 at a second end. The first portion 262 may be separated from the second portion 264 by a groove 266. The driver bit 260 may also include a securement or engagement feature 268 at the first end and a driver member or feature 270 at a second end. The second portion 264 may be inserted into the opening 258 of the coupling portion 256. When the driver bit 260 is inserted into the handle portion 252, the engagement feature 268 of the driver bit 260 may contact a bottom of the opening 258 and engage a corresponding securement feature (not shown) within the opening 258 of the handle portion 252. The driver feature 270 may be sized and shaped or configured to engage the tool engagement opening 124 of the cap member 120 to insert the cap member 120 onto the proximal portion 114 of the end member 110. The driver feature 270 may have, for example, a multi-lobed shape or other polygonal shape, including a hexagonal shape or a hexalobular drive feature.

Referring now to FIGS. 13-19, another implant 300 is shown. In addition to the above, the implant 300 also allows for screw-like implantation and temporary rigid fixation, then, after insertion, the implant 300 transitions to semi-constrained motion. The temporary rigid fixation of the implant 300 gives the fixed joint time to stabilize through healing and then over time allows physiologic motion to be restored. The area of allowed motion in implant 300 is in the space or gap between the fibula and tibia, where the subsequent risk of damage to bone is lower. The tension member or tether 350 mimics the interosseous ligament in both location and orientation. In addition, the components in the tibia and fibula protect the bone from abrasion from the tension member 350, and vice versa.

The implant 300 includes a proximal end 302, a distal end 304, and a coupling member 360 positioned between the proximal end 302 and the distal end 304. The implant 300 may also include a fibula member or end member 310, an anchor member or tibia member 330, a coupling member 360 positioned between and engaging the end member 310 and the anchor member 330, and a tension member 350 positioned within a cannulated opening that extends through the end member 310, anchor member 330 and the coupling member 360. The implant 300 may also include a compression cap 120 removably coupled to the end member 310. The compression cap 120 may be of the type described above with reference to implant 100 and which will not be described again here for brevity sake. The coupling member 360 may be positioned between the end member 310 and the anchor member 330 and allow for the anchor member 330 to be secured into the bones 210, 220 when the end member 310 is rotated. The tension member 350 may extend through a center of at least a portion of the aligned end member 310, the coupling member 360, and at least a portion of the anchor member 330.

The implant 300 may have a length of, for example, approximately 40 mm to 70 mm. In one embodiment, the length of the coupled end member 310 and coupling member 360 may remain constant, while the length of the anchor member 330 may be variable to correspond to the varying size of a patient's bones 210, 220. Alternatively, in another embodiment, the end member 310 and coupled cap 120 may, for example, be available in multiple lengths to correspond to the varying sizes of patient's bones 210, 220 and the lengths of the anchor member 330 and the coupling member 360 may remain constant. In yet another embodiment, both the coupled end member 310 and cap 120, as well as the anchor member 330 may be available in multiple lengths to allow for selection based on the size of the patient's bones 210, 220 and the coupling member 360 may remain constant. Therefore, the coupled end member 310 and cap 120 may have a length of, for example, between approximately 10 mm and 20 mm, the anchor member 330 may have a length of, for example, between approximately 20 mm and 60 mm, and the coupling member 360 may have a length of, for example, approximately 3 mm.

Figure 15:
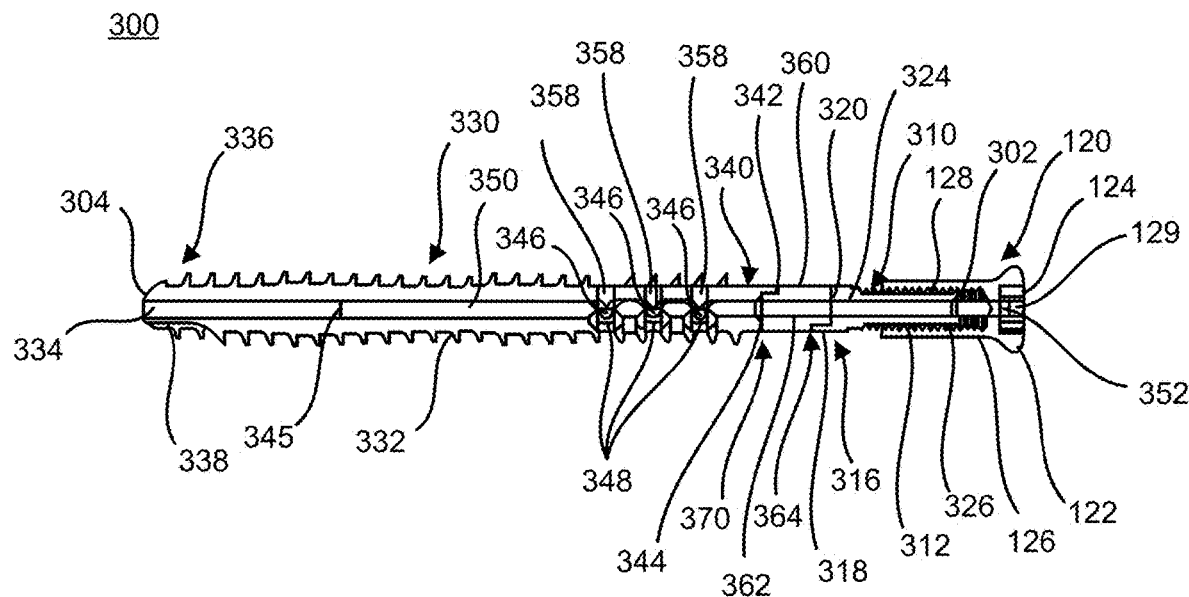
FIG. 15 is a first cross-sectional view of the implant of FIG. 13 taken along line 15-15 in FIG. 14, in accordance with an aspect of the present disclosure.
Figure 16:
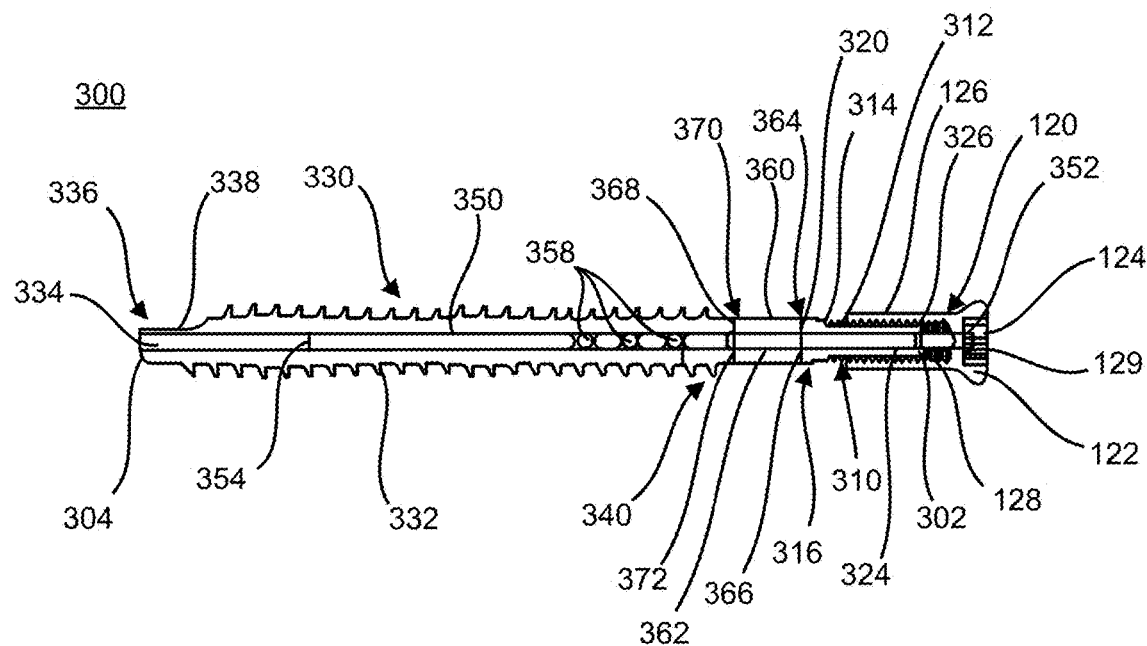
FIG. 16 is a second cross-sectional view of the implant of FIG. 13 taken along a longitudinal line perpendicular to line 15-15 in FIG. 14, in accordance with an aspect of the present disclosure.
Figure 17:
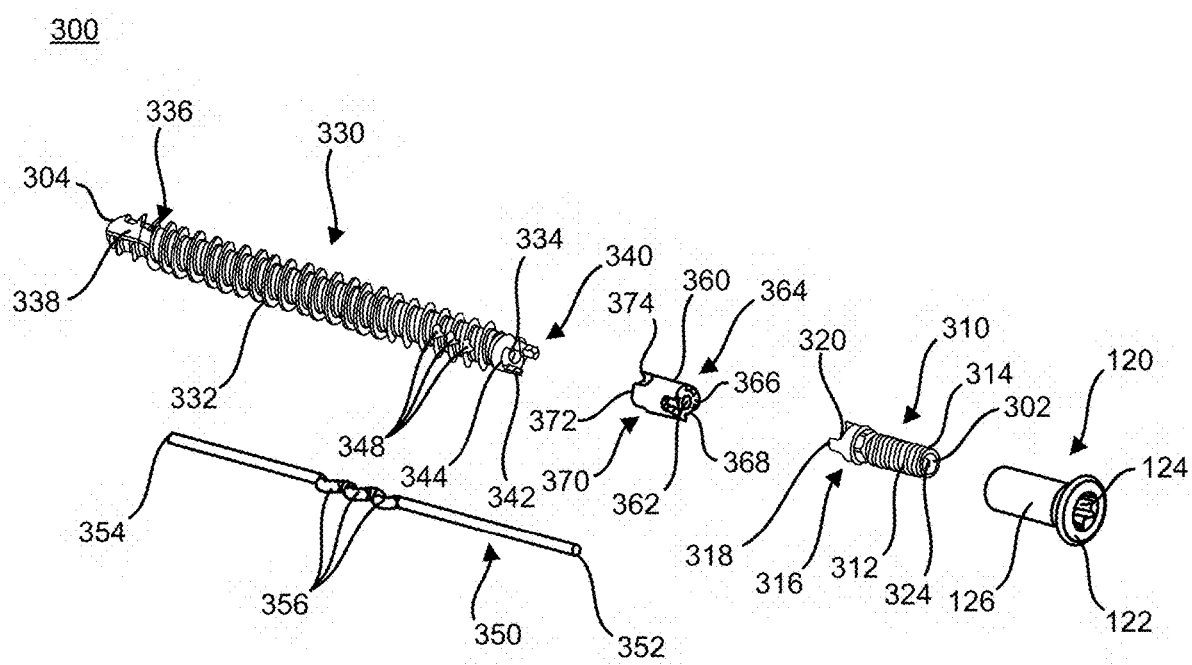
FIG. 17 is an exploded, first end perspective view of the implant of FIG. 13, in accordance with an aspect of the present disclosure.
Figure 18:
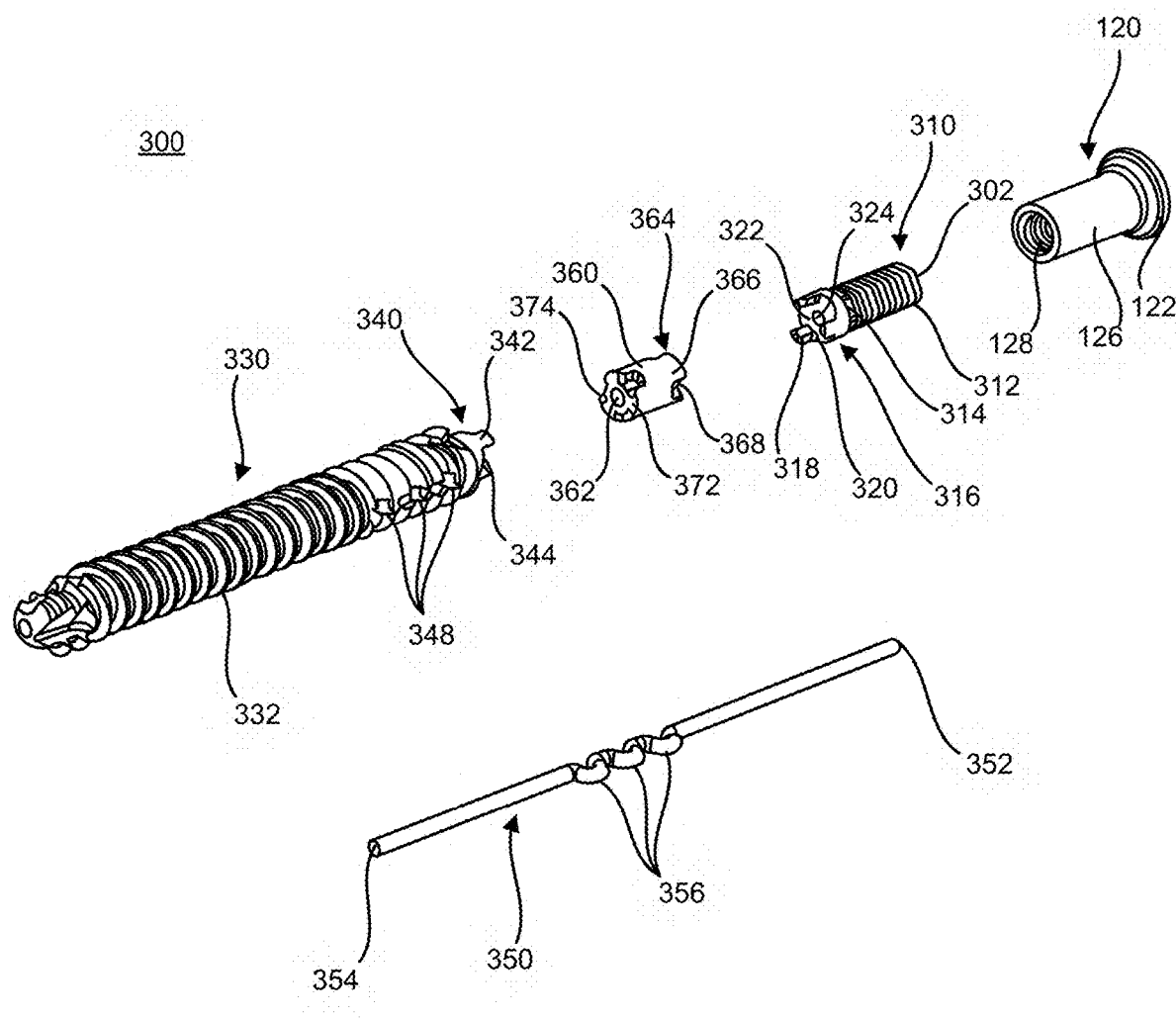
FIG. 18 is an exploded, second end perspective view of the implant of FIG. 13, in accordance with an aspect of the present disclosure.
Figure 19:
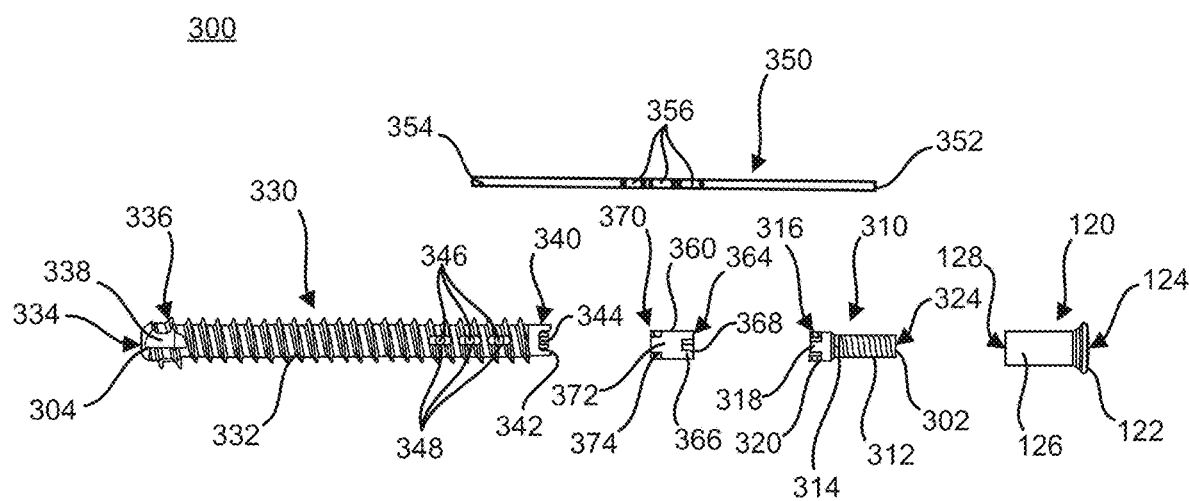
FIG. 19 is an exploded, side view of the implant of FIG. 13, in accordance with an aspect of the present disclosure.

As shown in FIGS. 13-19, the end member 310 may include a proximal portion 312 and a distal portion or engagement end 316. The proximal portion 312 may include, for example, threads from the proximal end 302 and extending toward the distal portion 316. The proximal portion 312 may also include at least one lateral removal member 314. The at least one lateral removal member 314 may be, for example, an external hexagonal drive feature, as shown in FIGS. 17-19. The at least one lateral removal member 314 may include surfaces for engaging an extraction instrument (not shown). The end member 310 may also include a through hole or cannulated opening 324. The cannulated opening 324 may extend through the entire end member 310 along the longitudinal axis of the end member 310.

The distal portion, engagement end or mating jaw 316 may include at least one protrusion or tooth 318 and at least one groove or recess 320, as shown in FIGS. 13-19. For example, the engagement end 316 may include three protrusions 318 alternating with three recesses 320. The end member 310 may also include an engagement surface 322 positioned between the at least one protrusion 318 for receiving a first end of the coupling member 360. In addition, the end member 310 may include an internal crimping feature 326, for example, a crimp ferrule positioned within the through hole 324 near the first end 302, as shown in FIGS. 15 and 16. The crimping feature 326 may secure a first end 352 of the tension member 350 to the end member 310. Alternatively, the end member 310 may include at least one transverse opening (not shown) in a first side of the proximal portion 312 and at least one slot, window, recess, aperture (not shown) inset into the interior diameter of the opening 324 and positioned opposite the at least one transverse opening (not shown). The at least one transverse opening (not shown) may be sized and shaped to receive a pin or engagement member (not shown). At least one pin (not shown) may be inserted through the at least one transverse opening (not shown) to engage the tension member 350 and push a portion of the tension member 350 into the opposing slots (not shown) securing the tension member 350 to the end member 310. The at least one slot (not shown) may be, for example, slightly offset from the at least one transverse opening (not shown) to provide additional securement of the tension member 350 to the end member 310. The pins (not shown) may also be coupled to the end member 310 by, for example, laser welding to prevent a pin from disengaging the end member 310 after insertion into a patient. The end member 310 may be made of, for example, titanium, stainless steel, polymer, or another like material as would be known by one of ordinary skill in the art.

With continued reference to FIGS. 13-19, the anchor member 330 may include a shaft portion or threaded shaft 332 with a through hole or cannulated opening 334 extending through the shaft portion 332 from a first end to a second end along the longitudinal axis of the anchor member 330. The anchor member 330 may also include an engagement end or mating jaw 340 at the first end and an insertion end 336 at the second end. The insertion end 336 may include at least one cutting element 338, for example, at least one cutting flute, as shown in at least FIGS. 13-19. The at least one cutting element 338 may be, for example, three cutting flutes. It is also contemplated that the cutting flutes at the insertion end 336 may be used as a removal feature if a medial approach is used to remove the anchor member 330. The shaft portion 332 may be, for example, threaded along the entire length of the shaft or only along a portion of the shaft. The engagement end or mating jaw 340 may include at least one protrusion or tooth 342 and at least one groove or recess 344, as shown in FIGS. 17-19. For example, the engagement end 340 may include three protrusions 342 alternating with three recesses 344.

The shaft portion 332 may also include at least one transverse opening 346 extending from an exterior surface of the shaft portion 332 into the through hole 334. The anchor member 330 may also include at least one slot, window, recess, or aperture 348 inset into the interior diameter of the through hole 334 or extending from an exterior surface of the shaft portion 332 into the through hole 334. The at least one slot 348 may be positioned, for example, opposite the at least one transverse opening 346. The at least one transverse opening 346 may be sized and shaped to receive at least one pin or engagement member 358. As shown in FIGS. 15 and 16, the pin 358 may be inserted through the at least one transverse opening 346 to engage the tension member 350 and push a portion 356 of the tension member 350 into the opposing at least one slot 348 securing the tension member 350 to the anchor member 330, as shown in FIGS. 15 and 16. Although not shown, the slots 348 may be, for example, slightly offset from the openings 346 to provide additional securement of the tension member 350 to the anchor member 330. The pins 358 may also be coupled to the anchor member 330 by, for example, laser welding to prevent a pin 358 from disengaging the anchor member 330 after insertion into a patient. The anchor member 330 may be made of, for example, titanium, stainless steel, polymer, and like materials as known by one of ordinary skill in the art.

Referring now to FIGS. 15-19, the tension member 350 may include a first end 352 and a second end 354. The first end 352 may be, for example, positioned within the cannulated opening 324 of the end member 310. The first end 352 may be secured to the end member 310 by, for example, an internal crimp ferrule 326 or, alternatively, pins (not shown) inserted through the at least one opening (not shown) to engage the tension member 350 and optionally an opposing slot (not shown), as described in greater detail above with respect to the openings 346 and slots 348 of the anchor member 330. The second end 354 may, for example, extend through a portion of the anchor member 330. The second end 354 may be secured to the anchor member 330 by, for example, at least one pin 358 inserted through the at least one opening 346 to engage the tension member 350 and at least one opposing slot 348, as shown in FIGS. 15 and 16 and described in greater detail above. The tension member 350 may be, for example, a braided suture, such as a size #5-#9 braided suture. The tension member 350 may be, for example, a single cross-section strand of suture or multiple loops.

As shown in FIGS. 13-19, the coupling member 360 may include a through hole or cannulated opening 362 extending through the coupling member 360 along a longitudinal axis of the coupling member 360. The coupling member 360 may also include a first engagement end or first mating jaw 364 at a first end and a second engagement end or second mating jaw 370 at a second end. The first engagement end 364 may include at least one protrusion or tooth 366 and at least one groove or recess 368, as shown in FIG. 17-19. For example, the first engagement end 364 may include three protrusions 366 alternating with three recesses 368. The second engagement end 370 may include at least one protrusion or tooth 372 and at least one groove or recess 374, as shown in FIGS. 17-19. For example, the second engagement end 370 may include three protrusions 372 alternating with three recesses 374. The protrusions 372 may be spaced, for example, 3 mm apart. The coupling member 360 may be made of, for example, a bioresorbable material, such as, PLLA, PGA, PLDA, PL-DLA, copolymers of each, resorbable calcium composites, and like materials as known by one of ordinary skill in the art.

As shown in FIGS. 13-16, the anchor member 330 is linked dynamically to the end member 310 by the tension member 350 and the coupling member 360. The implant 300 may be assembled by inserting the engagement end 316 of the end member 310 into the first engagement end 364 of the coupling member 360 and inserting the engagement end 340 of the anchor member 330 into the second engagement end 370 of the coupling member 360. The coupling member 360 will be positioned between the end member 310 and the anchor member 330. With the cannulated openings 324, 334, 362 of the end member 310, anchor member 330 and coupling member 360, respectively, aligned. Then, the tension member 350 may be inserted into the cannulated openings 324, 334, 362. The tension member 350 may be secured to the end member 310 by securing or tightening the crimp ferrule 326 around the tension member 350 and/or inserting at least one pin (not shown) through at least one transverse opening (not shown) in the end member 310 to engage and secure the tension member 350. The tension member 350 may also be secured to the anchor member 330 by inserting pins 358 through the at least one opening 346 in the anchor member 330 to engage and secure the tension member 350 or alternatively, by securing or tightening crimp members (not shown) around the tension member 350 at the second end. The assembled end member 310, coupling member 360, and anchor member 330 may be coupled together as shown in FIGS. 13-16 during insertion into a patient. After the tension member 350 is secured to the end member 310 and anchor member 330, the cap 120 may be coupled to the end member 310. For example, the threads of the opening 128 may engage the threads of the proximal portion 312 of the end member 310 to tighten the cap 120 onto the end member 310. The cap 120 may overlap the end member 310 a distance that corresponds with the amount of compression needed to create the desired space or gap or lateral gutter pressure between the bones 210, 220.

A method of inserting the implant 300 may optionally include positioning a plate 200 or washer (not shown) on a bone 220, for example, a fibula. The plate 200 or washer (not shown) may provide a buttress means for engaging the cap 120. The method may also include driving a k-wire or guide wire 202 through two bones 210, 220, for example, a fibula 220 and tibia 210, as shown in FIG. 7. Next, as shown in FIG. 8, a drill bit 204 of an instrument (not shown) may be inserted over the k-wire 202 by aligning a cannulated opening 206 in the drill bit 204 with the k-wire 202. The drill bit 204 may be used to drill an opening 208 through the bones 210, 220. The opening 208 may include, for example, an opening 212 in the tibia 210 and an opening 222 in the fibula 220. The opening 208 may also have a diameter, for example, that corresponds to the minor diameter of the anchor member 330. After the opening 208 is drilled, the drill bit 204 and optionally the k-wire 202 may be removed from the bones 210, 220, as shown in FIG. 9. Optionally, after removing the drill bit 204 from the bones 210, 220 and prior to removing the k-wire 202, measurements of the depth of the opening 208 may be taken using a cannulated depth gauge (not shown) inserted over the k-wire 202. Once the measurements are taken, the k-wire 202 may then be removed. Alternatively, the k-wire 202 may be removed from the bones 210, 220 and a standard depth gauge (not shown) may be used to take the measurements. For example, an overall or first depth measurement of the opening or drill hole 208, such as a measurement to the far cortex of the tibia, may be taken using a cannulated depth gauge, standard depth gauge or other like instrument. The surgeon may also take a second depth measurement of the portion of the opening 208 in the fibula using, for example, a standard depth gauge or like instrument, to determine the size of the end member 310 and cap 120. Then, an instrument, for example, insertion instrument 250 as shown in FIG. 12, may be used to insert the coupled end member 310, coupling member 360, anchor member 330 and tension member 350 of the implant 300 into the opening 208 in the bones 210, 220. The implant 300 may be inserted to position the anchor member 330 in the tibia 210, the end member 310 in the fibula 220, and the coupling member 360 in a tibiofibular space or gap. The torsional force applied to the end member 310 for inserting the implant 300 may be transmitted to the anchor member 330 through the coupling member 360. Next, the instrument may be removed from end member 310 of the implant 300. A cap 120 may then be aligned with and secured onto the end member 310 by engaging the threads of the opening 128 with the threads of the proximal portion 312 of the end member 310. As the cap 120 is tightened or loosened, the clear space between the bones 210, 220 is correspondingly adjusted to reduce or increase the space or gap between the bones 210, 220 and/or gutter pressure, while the coupling member 360 remains positioned in the space or gap. During insertion of the cap 120, the torque may be, for example, measured or limited to facilitate a desired compression range between the bones 210, 220. Finally, the surgical procedure may be completed.

After inserting the implant 300, the cap 120 may be, for example, optionally adjusted to release some of the compression between the bones 210, 220 based on a patient or doctor preference and/or surgical goals. Also after inserting the implant 300, the coupling member 360 will eventually fail leaving the end member 310 coupled to the anchor member 330 only by the tension member 350. The coupling member 360 may fail, for example, after at least a portion of the coupling member 360 is resorbed into the patient. Failure of the coupling member 360 will allow for semi-constrained motion between the tibia 210 and fibula 220 via the tension member 350. The flexibility of the tension member 350 may allow for diastatic motion of the implant 300. Thus, the implant 300 allows for the patient's physiologic motion to be restored in an anterior-posterior direction, a superior-inferior direction, as well as allowing for fibular rotation, at the joint based on the strength of the tension member 350 and the resorbable coupling 360.

As may be recognized by those of ordinary skill in the art based on the teachings herein, numerous changes and modifications may be made to the above-described and other embodiments of the present invention without departing from the scope of the invention. The end member, anchor member, breakaway portion, coupling member, tension member, cap and other components of the implant and/or system as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the implants and systems may include more or fewer components or features than the embodiments as described and illustrated herein. For example, the components and features of FIGS. 1-12 and FIGS. 13-19 may all be used interchangeably and in alternative combinations as would be modified or altered by one of skill in the art. Accordingly, this detailed description of the currently-preferred embodiments is to be taken in an illustrative, as opposed to limiting of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. An implant, comprising:
    a cap member comprising an internally threaded opening extending from a first end thereof;
    an anchor portion comprising external threads and a first end that defines a tip of the implant; and
    a coupling portion extending between the cap member and the anchor portion, the coupling portion including an externally threaded portion threadably coupled within the internally threaded opening of the cap member,
    wherein the cap member is longitudinally moveable along the coupling portion;
    wherein the coupling portion comprises a breakaway portion with a circumferential groove;
    wherein the coupling portion comprises outer planar surfaces circumferentially arranged about the coupling portion.

2. The implant of claim 1, wherein the cap member comprises:
    a shaft portion that defines the first end of the cap member and includes the internally threaded opening; and
    an enlarged head portion extending from the shaft portion that defines a second end of the cap member, the second end of the cap member defining a free end of the implant that opposes the tip of the implant.

3. The implant of claim 2, wherein the cap member further comprises a noncircular drive opening extending from the second end thereof.

4. The implant of claim 1, wherein the anchor portion comprises:
    a shaft portion with a first end portion, a second end portion and external threads; a proximal coupling portion extending from the first end portion of the shaft portion of the anchor member to the coupling portion; and
    a distal portion extending from the second end portion of the shaft portion of the anchor member and defining the first end of the anchor portion.

5. The implant of claim 4, wherein the distal portion comprises a plurality of circumferentially arranged longitudinally extending flutes positioned proximate to the first end of the anchor portion.

6. The implant of claim 4, wherein the coupling portion comprises:
    a coupling member coupled to the anchor portion; and
    an end member coupled to the coupling member, wherein the coupling member and the end member are separate and distinct components.

7. The implant of claim 6, wherein the coupling member is made of a bioresorbable material.

8. The implant of claim 6, wherein the end member comprises the externally threaded portion threaded portion threadably coupled within the internally threaded opening of the cap member, wherein the cap member is longitudinally moveable along the end member of the coupling portion.

9. The implant of claim 6, wherein the anchor portion comprises a second engagement end that opposes the first end thereof and engages a first engagement end of the coupling member, wherein each of the second engagement end of the anchor portion and the first engagement end of the coupling member include at least one projection and at least one recess, and wherein the at least one projection of the second engagement end of the anchor portion is positioned within the at least one recess of the first engagement end of the coupling member, and the at least one projection of the first engagement end of the coupling member is positioned within the at least one recess of the second engagement end of the anchor portion.

10. The implant of claim 9, wherein the coupling member comprises a second engagement end the opposes the first engagement end thereof and engages a first engagement end of the end member, wherein each of the second engagement end of the coupling member and the first engagement end of the end member include at least one projection and at least one recess, and wherein the at least one projection of the second engagement end of the coupling member is positioned within the at least one recess of the first engagement end of the coupling member is positioned within the at least one recess of the second engagement end of the coupling member.

11. The implant of claim 6, wherein the end member comprises a torque application feature comprising outer planar surfaces circumferentially arranged about the end member.

12. The implant of claim 6, wherein the anchor portion, the coupling member and the end member each include a cannulated opening that are aligned to form a through hole, and wherein the implant further comprises a tension member positioned within the through hole and including a first portion coupled to the end member and a second portion coupled to the anchor member.

13. The implant of claim 12, wherein the tension member comprises an elastic suture.

14. The implant of claim 12, wherein the anchor member further comprises at least one transverse opening extending from an exterior surface portion of the anchor member to the cannulated opening thereof, and at least one pin positioned within the at least one transverse opening and extending into the cannulated opening and in abutment with the second portion of the tension member to couple the second portion of the tension member and the anchor portion together.

15. The implant of claim 14, wherein the anchor further comprises at least one slot extending at least partially through the anchor member from an interior surface of the anchor member that forms the cannulated opening thereof, the at least one slot being aligned with the at least one transverse opening such that the at least one pin positioned within the at least one transverse opening deforms the second portion of the tension member into the at least one slot to couple the second portion of the tension member and the anchor portion together.

16. A system, comprising:
    an implant, comprising:
        a cap member comprising an internally threaded opening extending from a first end thereof;

an anchor portion comprising external threads and a first end that defines a tip of the implant; and
a coupling portion extending between the cap member and the anchor portion, the coupling portion including an externally threaded portion threadably coupled within the internally threaded opening of the cap member,
wherein the cap member is longitudinally moveable along the coupling portion;
wherein the coupling portion comprises a breakaway portion with a circumferential groove;
wherein the coupling portion comprises outer planar surfaces circumferentially arranged about the coupling portion;
an insertion instrument for coupling to the implant and rotating the implant about an axis of the implant; and
a plate with at least one aperture extending therethrough, wherein the entirety of the anchor portion, the entirety of the coupling portion and only a portion of the cap member are configured to pass through the at least one aperture of the implant.

17. An implant, comprising:
a cap member comprising an internally threaded opening extending from a first end thereof;
an anchor portion comprising external threads and a first end that defines a tip of the implant; and
a coupling portion extending between the cap member and the anchor portion, the coupling portion including an externally threaded portion threadably coupled within the internally threaded opening of the cap member, wherein the cap member is longitudinally moveable along the coupling portion;
a shaft portion with a first end portion, a second end portion and external threads; a proximal coupling portion extending from the first end portion of the shaft portion of the anchor member to the coupling portion; a distal portion extending from the second end portion of the shaft portion of the anchor member and defining the first end of the anchor portion;
wherein the coupling portion comprises: a coupling member coupled to the anchor portion; and an end member coupled to the coupling member, wherein the coupling member and the end member are separate and distinct components;
wherein the anchor portion comprises a second engagement end that opposes the first end thereof and engages a first engagement end of the coupling member, wherein each of the second engagement end of the anchor portion and the first engagement end of the coupling member include at least one projection and at least one recess, and wherein the at least one projection of the second engagement end of the anchor portion is positioned within the at least one recess of the first engagement end of the coupling member, and the at least one projection of the first engagement end of the coupling member is positioned within the at least one recess of the second engagement end of the anchor portion.

18. A system, comprising:
an implant, comprising:
a cap member comprising an internally threaded opening extending from a first end thereof;
an anchor portion comprising external threads and a first end that defines a tip of the implant; and
a coupling portion extending between the cap member and the anchor portion, the coupling portion including an externally threaded portion threadably coupled within the internally threaded opening of the cap member, wherein the cap member is longitudinally moveable along the coupling portion;
a shaft portion with a first end portion, a second end portion and external threads; a proximal coupling portion extending from the first end portion of the shaft portion of the anchor member to the coupling portion; a distal portion extending from the second end portion of the shaft portion of the anchor member and defining the first end of the anchor portion;
wherein the coupling portion comprises: a coupling member coupled to the anchor portion; and an end member coupled to the coupling member, wherein the coupling member and the end member are separate and distinct components;
wherein the anchor portion comprises a second engagement end that opposes the first end thereof and engages a first engagement end of the coupling member, wherein each of the second engagement end of the anchor portion and the first engagement end of the coupling member include at least one projection and at least one recess, and wherein the at least one projection of the second engagement end of the anchor portion is positioned within the at least one recess of the first engagement end of the coupling member, and the at least one projection of the first engagement end of the coupling member is positioned within the at least one recess of the second engagement end of the anchor portion;
an insertion instrument for coupling to the implant and rotating the implant about an axis of the implant; and
a plate with at least one aperture extending therethrough, wherein the entirety of the anchor portion, the entirety of the coupling portion and only a portion of the cap member are configured to pass through the at least one aperture of the implant.

* * * * *

UNITED STATES PATENT AND TRADEMARK OFFICE
CERTIFICATE OF CORRECTION

Page 1 of 1

PATENT NO. : 11,026,732 B2
APPLICATION NO. : 16/512807
DATED : June 8, 2021
INVENTOR(S) : Allard et al.

It is certified that error appears in the above-identified patent and that said Letters Patent is hereby corrected as shown below:

In the Claims

Column 18, Line 4: Claim 8, Delete "threaded portion threaded portion" and insert -- threaded portion --

Column 18, Line 39: Claim 10, Delete "member is positioned" and insert -- member is positioned within the at least one recess of the first engagement end of the coupling member, and the at least one projection of the first engagement end of the coupling member is positioned --

Signed and Sealed this
Twentieth Day of July, 2021

Drew Hirshfeld
*Performing the Functions and Duties of the
Under Secretary of Commerce for Intellectual Property and
Director of the United States Patent and Trademark Office*